(12) United States Patent
Thompson et al.

(10) Patent No.: US 8,193,158 B2
(45) Date of Patent: Jun. 5, 2012

(54) USE OF APOPTOSIS-SPECIFIC EIF-5A SIRNA TO DOWN REGULATE EXPRESSION OF PROINFLAMMATORY CYTOKINES TO TREAT SEPSIS

(75) Inventors: John E. Thompson, Waterloo (CA); Charles A. Dinarello, Denver, CO (US)

(73) Assignee: Senesco Technologies, Inc., New Brunswick, NJ (US)

( * ) Notice: Subject to any disclaimer, the term of this patent is extended or adjusted under 35 U.S.C. 154(b) by 1074 days.

(21) Appl. No.: 11/725,520

(22) Filed: Mar. 20, 2007

(65) Prior Publication Data

US 2009/0118207 A1    May 7, 2009

Related U.S. Application Data

(60) Provisional application No. 60/798,333, filed on May 8, 2006, provisional application No. 60/783,413, filed on Mar. 20, 2006.

(51) Int. Cl.
*C12N 15/11* (2006.01)

(52) U.S. Cl. ...................................................... 514/44 A

(58) Field of Classification Search .................. 514/44 A
See application file for complete search history.

(56) References Cited

U.S. PATENT DOCUMENTS

| 2006/0094677 A1 * | 5/2006 | Thompson et al. | ............. 514/44 |
| 2006/0154887 A1 * | 7/2006 | Thompson et al. | ............. 514/44 |
| 2006/0287265 A1 * | 12/2006 | Thompson et al. | ............. 514/44 |
| 2007/0154457 A1 * | 7/2007 | Thompson et al. | ........... 424/93.2 |
| 2007/0238691 A1 * | 10/2007 | Thompson et al. | ............. 514/44 |
| 2010/0168047 A9 * | 7/2010 | Thompson et al. | ......... 514/44 A |

FOREIGN PATENT DOCUMENTS

WO    WO 2005007853 A2 *    1/2005

\* cited by examiner

*Primary Examiner* — Brian Whiteman
(74) *Attorney, Agent, or Firm* — Morgan, Lewis & Bockius LLP

(57) ABSTRACT

The present invention relates to apoptosis specific eucaryotic initiation factor 5A (eIF-5A), referred to as apoptosis-specific eIF-5A or eIF5-A1, nucleic acids and polypeptides and methods for down regulating pro-inflammatory cytokines in a mammal by administering siRNA against eIF-5A1 to the mammal to treat/prevent sepsis and/or hemorrhagic shock.

7 Claims, 28 Drawing Sheets

AA [ CGG AAU GAC UUC CAG CUG A ] dTdT   SEQ ID NO. 3

Sense          5' CGGAAUGACUUCCAGCUGA dTdT 3'    SEQ ID NO. 4
anti-Sense 3' dTdTGCCUUACUGAAGGUCGACU 5'         SEQ ID NO. 5

FIG.19

NUCLEOTIDE ALIGNMENT OF HUMAN eIF5A1 (ACC. NM_001970) AND HUMAN eIF5A2 (ACC. NM_020390)

```
eIF5a1    1    ATGGCAGATG  ACTTGGACTT  CGAGACAGGA  GATGCAGGGG  CCTCAGCCAC
eIF5a2    1    ATGGCAGACG  AAATTGATTT  CACTACTGGA  GATGCCGGGG  CTTCCAGCAC eIF5a1   51    CTTCCAATG   CAGTGCTCAG  CATTACGtAA  GAATGGCTTT  GTGGTGCTCA
eIF5a2   51    TTACCCTATG  CAGTGCTCGG  CCTTGCGcAA  AAACGGCTTC  GTGGTGCTCA eIF5a1  101    AAGGCCGGCC  ATGtAAGATC  GTCGAGATGT  CTACTTCGAA  GACTGGCAAG
eIF5a2  101    AAGGACGACC  ATGCAAAATA  GTGGAGAtGT  CAACTTCCAA  AACTGGAAAG eIF5a1  151    CACGGCCACG  CCAAGGTCCA  TCTGGtTGGT  ATTGACATCT  TtACTGGGAA
eIF5a2  151    CAtGGTCATG  CCAAGGTTCA  CCTTGTtGGA  ATTGATATtI  TCACGGGGCAA eIF5a1  201    GAAATATGAA  GATATCTGCC  CGTCAACTCA  tAATATGGAT  GTCCCCAACA
eIF5a2  201    AAAATATGAA  GATATATTGT  CTTCCTACTCA  CAACATGGAT  GTTCCAAATA eIF5a1  251    TCAAAAGGAA  TGACTtCCAG  CTGATTGGCA  TCCAGGATGG  GTACTTATCA
eIF5a2  251    TTAAGAGAAA  TGATTatCAA  CTGATATGCA  TTCAAGATGG  TTACTTTCC eIF5a1  301    CTGCTCCagG  ACAGGGGGA   GGTACGACAG  GACCTTCGTC  TcCCTGAGGG
eIF5a2  301    CTGCTGacdG  AAACTGGTGA  AGTTCGTCGAG  GATCTTAAAC  TGCCAGAAGG eIF5a1  351    AGACCTTTGC  AAGGAGATTG  AGcgAAGTA   CGACTGTGGA  GAAGAGATCC
eIF5a2  351    TGAACTAGGC  AAAGAAATAG  AGggaAAATA  CAATGCAGGT  GAAGATGTAC eIF5a1  401    TGATCACGGT  GCTGTcCTGCC  ATGACAGAGG  AGGCAGCTGT  TGCAATCAAG
eIF5a2  401    AGGTGTCTGT  CATGtgTGCA  ATGAGTGAAG  AATATGCTGT  AGCCATAAAA eIF5a1  451    GCCatgGCAA  AATAa                           SEQ ID NO. 6
eIF5a2  451    CCCt -GCAA  ATAA-                           SEQ ID NO. 7
```

FIG. 22

AMINO ACID ALIGNMENT OF HUMAN eIF5a1 (ACC. NM_001970) AND HUMAN eIF5a2 (ACC. NM_020390)

```
eIF5a1         MADDLDFETG DAGASATFPM QCSALRKNGF VVLKGRPCKI VEHSASKTGK
eIF5a2    1    MADEIDFTTG DAGASSTYPM QCSALRKNGF VVLKGRPCKI VEHSTSKTGK eIF5a1   51    HGHAKVHLVG IDIFTGKKYE DICPSTHNMD VPNIKRNDFQ LIGIQDGYLS
eIF5a2   51    HGHAKVHLVG IDIFTGKKYE DICPSTHNMD VPNIKRNDYQ LICIQDGYLS eIF5a1  101    LLQDSGEVPE DLRLPEGDLG KEIEQKYDCG EEILITLLSA MTEEAAVAIK
eIF5a2  101    LLTETGEVRE DLKLPEGELG KEIEGKYNAG EDVQVSVMCA MSEEYAVAIK eIF5a1  151    amak    SEQ ID NO. 8
eIF5a2  151    pck·    SEQ ID NO. 9
```

FIG.23

| ANTISENSE OLIGO 1 | 5'- CCT GTC TCG AAG TCC AAG TC -3' | SEQ ID NO. 10 |
| TARGET | 5'- GACTTGGACTTCGAGACAGG -3' | SEQ ID NO. 11 |
| ANTISENSE OLIGO 2 | 5'- GGA CCT TGG CGT GGC CGT GC -3' | SEQ ID NO. 12 |
| TARGET | 5'- GCACGGCC ACGCCAAGGTCC -3' | SEQ ID NO. 13 |
| ANTISENSE OLIGO 3 | 5'- CTC GTA CCT CCC CGC TCT CC -3' | SEQ ID NO. 14 |
| TARGET | 5'- GGACAGCGG GGAGGTACGA -3' | SEQ ID NO. 15 |

```
   1 ggcacgaggg tagagcggc ggcggcggg gcagcggct cggagcagc ggttggctc
  61 gggcgacg gacggctcg agtcagtgcg ttcggcgag ttggaatcga agcctcttaa
 121 aatgcagat cctgaaa tcgaaga agatacaggg gcctcagca ccttcccaat
 181 gcagtgctca gcattacgta agaatggctt tgtgtactc aaggccagc catgtaagat
 241 cgtcgagatg tctacttcga agactgcaa ttcaggcca tccaggttcc atctggttgg
 301 tattgacatc tttactggga agaaatgaa agatatctgc ccgtcaactc ataatatgaa
 361 tgtccccaac atcaaagga ataacttcca gctgattggc atccaggatg ggtacctatc
 421 actgctcct gccttgagga ggagccttcgt ctccctgagg gagaccttgg
 481 caaggagatt gagcagaagt acgactgtgg agaagagatc ctgatcacgg tgctgtctgc
 541 catgacagag gaggcagctg ttgcaatcaa gccatgca aaataactgg ctcccaggat
 601 ggcggtggtg gcagcagtga tcctctgaac ctgcagaggc ccctcccg agcctggct
 661 ggctctggcc cggtcctaag ctggactcct cctacacaat ttattgacg tttattttg
 721 gtttcccca ccccctcaat ctgtcgggga gccctgcc ttcacctagc tcccttgcc
 781 aggagcgagc gaagctgtgg ccttggtgaa gctgccctcc tcttctcccc tcacactaca
 841 gccctggtga ggagaaggg ggtggtgct gcttgtgtt tagtctttt tttttttt
 901 tttttttttt aattcaatc tggaatcaga aagcggtgga tctggcaaa tggtccttgt
 961 gccctcccca ctcatccctg gtctggtccc ctgttgccca tagcccttta ccctgagcac
1021 cacccaaca gactgggac cagccccctc gcctgcctgt gtctctcccc aaaccccttt
1081 aatgcggag ggaagaggag gagagagag ggacctgcc ccctcctcag gcatctggaa
1141 gggccctgcc ccatgggct ttaccttcc ctgcgggctc tctcccgac acattgtta
1201 aaatcaaacc tgaataaaac tacaagttta atatgaaaaa aaaaaaaaa aaaaaaaaa
1261 aaaaaaaaaa aaaaaaaaa aaaaaaaaa aaaaaaaaa aaaaaaaaa SEQ ID NO. 16
```

DESIGN OF siRNAs AGAINST eIF5A1

POSITION OF siRNAs WITHIN eIF5A1 mRNA
* TRANSLATION START AND STOP ARE BOLD AND UNDERLINED

```
   1 ggcacgagg tagaggcagc gacggcgacg gcagcgggct cggaggcagc ggttggctc
  61 gcggcgacg gacgggtcg agtcagtgcg ttcgcgcgag ttggaatcga agcctcttaa
 121 atgcagat gactggact tcgagacagg agatgcaggg gcctcagcca cctcccaat
 181 gcagtgctca gcattagta agatggctt tgtggtgctc aaggccggc catgtaggat
 241 catcgaatg tctacttcga agactggcaa gcacggccac gccaggtcc atctgattgg
 301 tattgacatc ttactggaa agaaatatga agatatctgc ccgtcaactc ataatatgga
 361 tgtccccaac atcgaaacga gtaacttcga actaattgcc atccaggatg ggtacctatc
 421 actctccag gaccgcggg aggtacgagg agaccttgt ctccctgagg gagacttgg
 481 caaggagatt gagcagaagt acgactgtgg agaagagatc ctgatcacgg tgctgtctgc
 541 catgacagag gaggcagctg ttgcaatcaa ggccatggca aaatga tgg ctcccaggat
 601 gcggtggtg gcagcagtga tcctctgaac ctgcagaggc ccctcccg agctggcct
 661 ggctctggcc cggtcctaag cagaatcct ccttacgcat ttatttgacg ttttattttg
 721 gttttcccca ccccctcaat ctgtgaggga gccctgccc ttcacctagc tccttgcc
 781 aggagcgagc gaagctgtgg ccttagtgaa gctgcctcc tcttctcccc tcacactaca
 841 gccctggtgg ggagaaggg ggtgggtgct gctgtgtgtt tagtcttttt tttttttttt
 901 tttttttttt aaatcaatc tggaatcaga aagcggtgga ttctggcaaa tggtccttgt
 961 gccctcccca ctcatccctg gtctggtccc ctgttgccca tagcccttta ccctgagcac
1021 cacccaaca gactggggac cagcccctc gcctgcctgt gtctctcccc aaaccccttt
1081 agatgggag ggaagaggagagaggag ggaactgcc cctcctcag gcatctggaa
1141 gggcctgcc ccatggct ttaccttcc ctgcgggctc tctccccgac acattgtta
1201 aaatcaaacc tgaataaaac tacaagttta atatgaaaaa aaaaaaaaaa aaaaaaaaa
1261 aaaaaaaaaa aaaaaaaaaa aaaaaaaaaa aaaaaaaaaa aaaaaaaa         SEQ ID NO. 16
``` siRNA # 1 TARGET
siRNA # 2 TARGET
siRNA # 3 TARGET
siRNA # 4 TARGET

POSITION OF siRNA TARGETS AND SEQUENCES AND BLAST RESULTS
siRNA # 1 TARGET POSITION 375 TO 395 bp (POSITION 254 TO 274 bp RELATIVE TO START) % G/C = 39.1 BLAST = NONE BUT eIF5A

TARGET   5' AACAGGAATGACTTCCAGCTGA 3'    SEQ ID NO. 20 siRNA    5' AAGGAAUGACUUCCAGCUGAdTdT 3'  SEQ ID NO. 21
         3' dTdTUUCCUUACUGAAGGUCGACU 5'  SEQ ID NO. 22

FIG. 26A siRNA # 2 TARGET POSITION 236 TO 256 (115 TO 135 bp RELATIVE TO START) %
G/C = 43.4 BLAST - IDENTICAL TO HYPOTHETICAL PROTEIN IN RAT

TARGET    5' AA(GATCGTCGAGATGTCTACT) 3'   SEQ ID NO. 23 siRNA     5' AAGAUCGUCGAGAUGUCUACUdTdT 3'  SEQ ID NO. 24
          3' dTdTUUCUAGCAGCUCUACAGAUGA 5'  SEQ ID NO. 25 siRNA # 3 TARGET POSITION 284 TO 304 (163 TO 183 bp RELATIVE TO START) %
G/C = 43.4 BLAST - NONE BUT eIF5A

TARGET    5' AA(GGTCCATCTGGTTGGTATT) 3'   SEQ ID NO. 26 siRNA     5' AAGGUCCAUCUGGUUGGUAUUdTdT 3'  SEQ ID NO. 27
          3' dTdTUUCCAGGUAGACCAACCAUAA 5'  SEQ ID NO. 28 siRNA # 4 TARGET POSITION 678 TO 698 (3'UTR:POSITION 557 TO 577 bp
RELATIVE TO START) % G/C = 48 BLAST - NONE BUT eIF5A

TARGET    5' AA(GCTGGACTCCTCCTACACA) 3'   SEQ ID NO. 29 siRNA     5' AAGCUGGACUCCUCCUACACAdTdT 3'  SEQ ID NO. 30
          3' dTdTUUCGACCUGAGGAGGAUGUGU 5'  SEQ ID NO. 31 siRNA # 5 CONTROL;REVERSE SEQUENCE OF siRNA # 1

% G/C = 39.1 BLAST -GOOD, NO MORE THAN 17/23 % IDENTITY

TARGET    5' AA(AGTCGACCTTCAGTAGGA) 3'   SEQ ID NO. 32 siRNA     5' AAAGUCGACCUUCAGUAGGAdTdT 3'  SEQ ID NO. 33
          3' dTdTUUCAGCUGGAAGUCAUCCU 5'   SEQ ID NO. 34

FIG. 26B

```
siRNA #1   target 5' AA(AGGAATGACTTCCAGCTGA)TT 3'   SEQ ID NO. 35
siRNA #2   target 5' AA(GATCGTCGAGATGTCTACT)TC 3'   SEQ ID NO. 36
siRNA #3   target 5' AA(GGTCCATCTGTTGGTATT)GA 3'    SEQ ID NO. 37
siRNA #4   target 5' AA(GCTGGACTCCTCCTACACA)AT 3'   SEQ ID NO. 38
siRNA #5   REVERSE OF siRNA #1 5' AA(AGTCGACCTTCAGTAGGA)TT 3'  SEQ ID NO. 39
```

```
   1  ggcacgaggg tagaggcagc ggcagcgacg gcagcggact cggaggcagc ggttgggctc
  61  gggggaggg  gacggatcg  aatcagtgcg ttgcgcgga  ttggaatgga agcctcttaa
 121  aatgcagat  gactggact  tcgagacagg agatgcaggg ggctcagcca cctcccaat
 181  gcagtgctca gcattagta  agaatggctt tgtggtgctc aaagccggc catgtgat
 241  cgtggaat   tctactta   agactggcaa gcacggccac gc...      tcgtattgc
 301  catc atc   ttactggga  agaaatga   agatatctgc cgtcaactc  ataatatgga
 361  tgtcccaac  atc ..... ...... ....  ........  atccaggatg gtacctatc
 421  actgctccag gacagaggg  aggtacgaga ggacttgt   ctccctgagg gagacctgg
 481  caaggagatt gagcagaagt acgactgtgg agaagagatc ctgatcaagg tgctgtctgc
 541  catgacagag gaggcagctg ttgcaatcaa ggccatggca aaataactgg ctcccaggat
 601  ggcggtgtg  gcagcagtga tcctctgaac ctccggagc  ccctcccg   agcctggct
 661  ggctctggcc cggtcc .... ........ ..........  ttattgacg  tttattttg
 721  gttttccca  ccccctcaat ctgtcggga  gccctgcc   ttcacctagc tcccttggcc
 781  aggacgagc  gaagctgtgg cctggtgaa  gctgcctcc  tcttctccc  tcaactca
 841  gccctggtgg gggagaagag ggtgggtgct gcttgtggtt tagtcttttt ttttttttt
 901  tttttttttt aaattcaatc tggaatcaga aagcggtgga ttctgccaaa tggtccttgt
 961  gcctcccca  ctcatccctg gtctggtccc ctgttgccca tagccttta  ccctgagcac
1021  cacccaaca  gactgggac  cagccccctc gcctgcctgt gtctctccc  aaacccttt
1081  agatggggag ggagggggag gagagggag  ggacctgcc  cctcctcag  gcatctggga
1141  ggccctgcc  cccatggct  ttaccttcc  ctgcggctc  tctcccgac  acatttgtta
1201  aaatcaaacc tgaataaaac tacagttta  atatgaaaa  aaaaaaaaa  aaaaaaaaa
1261  aaaaaaaaa  aaaaaaaa   aaaaaaaaa  aaaaaaaaa  aaaaaaaa  SEQ ID NO. 16
```

FIG. 27

```
                        SEQUENCE LISTING

<160> NUMBER OF SEQ ID NOS: 39

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
cggaaugacu uccagcuga                                                 19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ucagcuggaa gucauuccg                                                 19

<210> SEQ ID NO 3
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic construct
<220> FEATURE:
<223> OTHER INFORMATION: Description of Artificial Sequence: Synthetic
      construct

<400> SEQUENCE: 3
aacggaauga cuuccagcug att                                            23

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic construct
<220> FEATURE:
<223> OTHER INFORMATION: Description of Artificial Sequence: Synthetic
      construct

<400> SEQUENCE: 4
cggaaugacu uccagcugat t                                              21

<210> SEQ ID NO 5
<211> LENGTH: 21
```

```
<212> TYPE: DNA
<213> ORGANISM: Artificial Sequence
<220> FEATURE:
<223> OTHER INFORMATION: Description of Combined DNA/RNA Molecule:
      Synthetic construct
<220> FEATURE:
<223> OTHER INFORMATION: Description of Artificial Sequence: Synthetic
      construct

<400> SEQUENCE: 5
ucagcuggaa gucauuccgt t                                               21

<210> SEQ ID NO 6
<211> LENGTH: 465
<212> TYPE: DNA
<213> ORGANISM: Homo sapiens

<400> SEQUENCE: 6
atggcagatg acttggactt cgagacagga gatgcagggg cctcagccac cttcccaatg     60
cagtgctcag cattacgtaa gaatggcttt gtggtgctca aggccggcc atgtaagatc     120 gtcgagatgt ctacttcgaa gactggcaag cacggccacg ccaaggtcca tctggttggt    180
attgacatct ttactgggaa gaaatatgaa gatatctgcc cgtcaactca taatatggat    240
gtccccaaca tcaaaaggaa tgacttccag ctgattggca tccaggatgg gtacctatca    300
ctgctccagg acagcgggga ggtacgagag gaccttcgtc tccctgaggg agaccttggc    360
aaggagattg agcagaagta cgactgtgga gaagagatcc tgatcacggt gctgtctgcc    420
atgacagagg aggcagctgt tgcaatcaag gccatggcaa ataa                     465

<210> SEQ ID NO 7
<211> LENGTH: 462
<212> TYPE: DNA
<213> ORGANISM: Homo sapiens

<400> SEQUENCE: 7
atggcagacg aaattgattt cactactgga gatgccgggg cttccagcac ttaccctatg     60
cagtgctcgg ccttgcgcaa aaacggcttc gtggtgctca aggacgacc atgcaaaata    120 gtggagatgt caacttccaa aactggaaag catggtcatg ccaaggttca ccttgttgga    180
attgatattt tcacgggcaa aaaatatgaa gatatttgtc cttctactca caacatggat    240
gttccaaata ttaagagaaa tgattatcaa ctgatatgca ttcaagatgg ttacctttcc    300
ctgctgacag aaactggtga agttcgtgag gatcttaaac tgccagaagg tgaactaggc    360
aaagaaatag agggaaaata caatgcaggt gaagatgtac aggtgtctgt catgtgtgca    420
atgagtgaag aatatgctgt agccataaaa ccctgcaaat aa                      462

<210> SEQ ID NO 8
<211> LENGTH: 154
<212> TYPE: PRT
<213> ORGANISM: Homo sapiens

<400> SEQUENCE: 8

Met Ala Asp Asp Leu Asp Phe Glu Thr Gly Asp Ala Gly Ala Ser Ala
1               5                   10                  15

Thr Phe Pro Met Gln Cys Ser Ala Leu Arg Lys Asn Gly Phe Val Val
            20                  25                  30

Leu Lys Gly Trp Pro Cys Lys Ile Val Glu Met Ser Ala Ser Lys Thr
        35                  40                  45

Gly Lys His Gly His Ala Lys Val His Leu Val Gly Ile Asp Ile Phe
    50                  55                  60
```

-continued

Thr Gly Lys Lys Tyr Glu Asp Ile Cys Pro Ser Thr His Asn Met Asp
 65                  70                  75                  80

Val Pro Asn Ile Lys Arg Asn Asp Phe Gln Leu Ile Gly Ile Gln Asp
                 85                  90                  95

Gly Tyr Leu Ser Leu Leu Gln Asp Ser Gly Glu Val Pro Glu Asp Leu
            100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Leu Leu Ser Ala Met Thr Glu Glu
130                 135                 140

Ala Ala Val Ala Ile Lys Ala Met Ala Lys
145                 150

<210> SEQ ID NO 9
<211> LENGTH: 153
<212> TYPE: PRT
<213> ORGANISM: Homo sapiens

<400> SEQUENCE: 9

Met Ala Asp Glu Ile Asp Phe Thr Thr Gly Asp Ala Gly Ala Ser Ser
1               5                   10                  15

Thr Tyr Pro Met Gln Cys Ser Ala Leu Arg Lys Asn Gly Phe Val Val
                20                  25                  30

Leu Lys Gly Arg Pro Cys Lys Ile Val Glu Met Ser Thr Ser Lys Thr
            35                  40                  45

Gly Lys His Gly His Ala Lys Val His Leu Val Gly Ile Asp Ile Phe
        50                  55                  60

Thr Gly Lys Lys Tyr Glu Asp Ile Cys Pro Ser Thr His Asn Met Asp
 65                 70                  75                  80

Val Pro Asn Ile Lys Arg Asn Asp Tyr Gln Leu Ile Cys Ile Gln Asp
                85                  90                  95

Gly Tyr Leu Ser Leu Leu Thr Glu Thr Gly Glu Val Arg Glu Asp Leu
            100                 105                 110

Lys Leu Pro Glu Gly Leu Gly Lys Glu Ile Glu Gly Lys Tyr Asn
        115                 120                 125

Ala Gly Glu Asp Val Gln Val Ser Val Met Cys Ala Met Ser Glu Glu
130                 135                 140

Tyr Ala Val Ala Ile Lys Pro Cys Lys
145                 150

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cctgtctcga agtccaagtc                                               20

<210> SEQ ID NO 11
<211> LENGTH: 20
<212> TYPE: DNA
<213> ORGANISM: Homo sapiens

<400> SEQUENCE: 11
gacttggact tcgagacagg                                               20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 12
ggaccttggc gtggccgtgc                                                    20

<210> SEQ ID NO 13
<211> LENGTH: 20
<212> TYPE: DNA
<213> ORGANISM: Homo sapiens

<400> SEQUENCE: 13
gcacggccac gccaaggtcc                                                    20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 14
ctcgtacctc cccgctctcc                                                    20

<210> SEQ ID NO 15
<211> LENGTH: 19
<212> TYPE: DNA
<213> ORGANISM: Homo sapiens

<400> SEQUENCE: 15
ggacagcggg gaggtacga                                                     19

<210> SEQ ID NO 16
<211> LENGTH: 1309
<212> TYPE: DNA
<213> ORGANISM: Homo sapiens

<400> SEQUENCE: 16
ggcacgaggg tagaggcggc ggcggcggcg gcagcgggct cggaggcagc ggttgggctc         60
gcggcgagcg gacggggtcg agtcagtgcg ttcgcgcgag ttggaatcga agcctcttaa       120
aatggcagat gacttggact tcgagacagg agatgcaggg gcctcagcca ccttcccaat       180
gcagtgctca gcattacgta agaatggctt tgtggtgctc aaaggccggc catgtaagat       240
cgtcgagatg tctacttcga agactggcaa gcacggccac gccaaggtcc atctggttgg       300
tattgacatc tttactggga agaaatatga agatatctgc cgtcaactc ataatatgga        360 tgtccccaac atcaaaagga atgacttcca gctgattggc atccaggatg gtacctatc       420 actgctccag gacagcgggg aggtacgaga ggaccttcgt ctccctgagg gagaccttgg       480
caaggagatt gagcagaagt acgactgtgg agaagagatc ctgatcacgg tgctgtctgc       540
catgacagag gaggcagctg ttgcaatcaa ggccatggca aaataactgg ctcccaggat       600
ggcggtggtg gcagcagtga tcctctgaac ctgcagaggc cccctccccg agcctggcct       660
ggctctggcc cggtcctaag ctggactcct cctacacaat ttatttgacg ttttattttg       720
gttttcccca cccccctcaat ctgtcgggga gcccctgccc ttcacctagc tcccttggcc     780

```
aggagcgagc gaagctgtgg ccttggtgaa gctgccctcc tcttctcccc tcacactaca    840
gccctggtgg gggagaaggg ggtgggtgct gcttgtggtt tagtcttttt tttttttttt    900
tttttttttt aaattcaatc tggaatcaga aagcggtgga ttctggcaaa tggtccttgt    960
gccctcccca ctcatccctg gtctggtccc ctgttgccca tagccctttta ccctgagcac   1020 caccccaaca gactggggac cagccccctc gcctgcctgt gtctctcccc aaaccccttt   1080
agatggggag ggaagaggag gagaggggag gggacctgcc ccctcctcag gcatctggga   1140
gggccctgcc cccatgggct ttaccccttcc ctgcgggctc tctccccgac acatttgtta  1200
aaatcaaacc tgaataaaac tacaagttta atatgaaaaa aaaaaaaaaa aaaaaaaaa   1260 aaaaaaaaaa aaaaaaaaaa aaaaaaaaaa aaaaaaaaa aaaaaaaa              1309
```

```
<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gcacggccac gccaaggtc                                                  19

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ggacagcggg gaggtacgag                                                 20

<210> SEQ ID NO 19
<211> LENGTH: 1299
<212> TYPE: DNA
<213> ORGANISM: Homo sapiens

<400> SEQUENCE: 19
ggcacgaggg cggcggcggc ggtagaggcg gcggcggcgg cggcagcggg ctcggaggca     60
gcggttgggc tcgcggcgag cggacggggt cgagtcagtg cgttcgcgcg agttggaatc   120
gaagcctctt aaaatggcag atgacttgga cttcgagaca ggagatgcag gggcctcagc   180
caccttccca atgcagtgct cagcattacg taagaatggc tttgtggtgc tcaaaggccg   240
gccatgtaag atcgtcgaga tgtctacttc gaagactggc aagcacggcc acgccaaggt   300
ccatctggtt ggtattgaca tctttactgg gaagaaatat gaagatatct gcccgtcaac   360
tcataatatg gatgtcccca acatcaaaag gaatgacttc cagctgattg gcatccagga   420
tgggtaccta tcactgctcc aggacagcgg ggaggtacga ggaccttc gtctccctga    480 gggagacctt gcaaggaga ttgagcagaa gtacgactgt ggagaagaga tcctgatcac   540
ggtgctgtct gccatgacag aggaggcagc tgttgcaatc aaggccatgg caaaataact   600
ggctcccagg atggcggtgg tggcagcagt gatcctctga acctgcagag gcccctcccc   660
cgagcctggc ctggctctgg cccggtccta agctggactc ctcctacaca atttatttga   720
cgttttattt tggttttccc cacccccctca atctgtcggg gagcccctgc ccttcaccta   780
gctcccttgg ccaggagcga gcgaagctgt ggccttggtg aagctgccct cctcttctcc   840
```

-continued

```
cctcacacta cagccctggt gggggagaag gggtggtg ctgcttgtgg tttagtcttt      900
tttttttttt tttttttttt tttaaattca atctggaatc agaaagcggt ggattctggc      960
aaatggtcct tgtgccctcc ccactcatcc ctggtctggt ccctgttgc ccatagccct     1020 ttaccctgag caccacccca acagactggg gaccagcccc ctcgcctgcc tgtgtctctc    1080
cccaaacccc tttagatggg gagggaagag gaggagaggg gagggaccct gccccctcct    1140
caggcatctg ggagggccct gccccatgg gctttaccct tccctgcggg ctctctcccc     1200
gacacatttg ttaaaatcaa acctgaataa aactacaagt ttaatatgaa aaaaaaaa      1260 aaaaaaaaaa aaaaaaaaaa aaaaaaaaaa aaaaaaaaa                           1299
```

<210> SEQ ID NO 20
<211> LENGTH: 21
<212> TYPE: DNA
<213> ORGANISM: Homo sapiens

<400> SEQUENCE: 20
aaaggaatga cttccagctg a                                                21

<210> SEQ ID NO 21
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 21
aaaggaauga cuuccagcug att                                              23

<210> SEQ ID NO 22
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 22
ucagcuggaa gucauuccuu utt                                              23

<210> SEQ ID NO 23
<211> LENGTH: 21
<212> TYPE: DNA
<213> ORGANISM: Homo sapiens

<400> SEQUENCE: 23
aagatcgtcg agatgtctac t                                                21

<210> SEQ ID NO 24
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

```
<400> SEQUENCE: 24
aagaucgucg agaugucuac utt                                           23

<210> SEQ ID NO 25
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 25
aguagacauc ucgacgaucu utt                                           23

<210> SEQ ID NO 26
<211> LENGTH: 21
<212> TYPE: DNA
<213> ORGANISM: Homo sapiens

<400> SEQUENCE: 26
aaggtccatc tggttggtat t                                             21

<210> SEQ ID NO 27
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 27
aagguccauc ugguugguau utt                                           23

<210> SEQ ID NO 28
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 28
aauaccaacc agauggaccu utt                                           23

<210> SEQ ID NO 29
<211> LENGTH: 21
<212> TYPE: DNA
<213> ORGANISM: Homo sapiens

<400> SEQUENCE: 29
aagctggact cctcctacac a                                             21

<210> SEQ ID NO 30
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
```

```
<220> FEATURE:
<223> OTHER INFORMATION: Description of Artificial Sequence: Synthetic
      oligonucleotide

<400> SEQUENCE: 30
aagcuggacu ccuccuacac att                                              23

<210> SEQ ID NO 31
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 31
uguguaggag gaguccagcu utt                                              23

<210> SEQ ID NO 32
<211> LENGTH: 21
<212> TYPE: DNA
<213> ORGANISM: Homo sapiens

<400> SEQUENCE: 32
aaagtcgacc ttcagtaagg a                                                21

<210> SEQ ID NO 33
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 33
aaagucgacc uucaguaagg att                                              23

<210> SEQ ID NO 34
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 34
uccuuacuga aggucgacuu utt                                              23

<210> SEQ ID NO 35
<211> LENGTH: 23
<212> TYPE: DNA
<213> ORGANISM: Homo sapiens

<400> SEQUENCE: 35
aaaggaatga cttccagctg att                                              23

<210> SEQ ID NO 36
<211> LENGTH: 23
<212> TYPE: DNA
```

```
<213> ORGANISM: Homo sapiens

<400> SEQUENCE: 36
aagatcgtcg agatgtctac ttc                                              23

<210> SEQ ID NO 37
<211> LENGTH: 23
<212> TYPE: DNA
<213> ORGANISM: Homo sapiens

<400> SEQUENCE: 37
aaggtccatc tggttggtat tga                                              23

<210> SEQ ID NO 38
<211> LENGTH: 23
<212> TYPE: DNA
<213> ORGANISM: Homo sapiens

<400> SEQUENCE: 38
aagctggact cctcctacac aat                                              23

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
aaagtcgacc ttcagtaagg att                                              23
```

USE OF APOPTOSIS-SPECIFIC EIF-5A SIRNA TO DOWN REGULATE EXPRESSION OF PROINFLAMMATORY CYTOKINES TO TREAT SEPSIS

RELATED APPLICATIONS

This application claims priority to U.S. provisional application 60/798,333, filed May 8, 2006 and U.S. provisional application 60/783,413, filed Mar. 20, 2006, both of which are herein incorporated by reference in their entirety.

FIELD OF THE INVENTION

The present invention relates to apoptosis-specific eucaryotic initiation factor ("eIF-5A") or referred to as "apoptosis-specific eIF-5A" or "eIF-5A1" and the use of siRNA against eIF-5A1 to down regulate expression of pro-inflammatory cytokines.

BACKGROUND OF THE INVENTION

Apoptosis is a genetically programmed cellular event that is characterized by well-defined morphological features, such as cell shrinkage, chromatin condensation, nuclear fragmentation, and membrane blebbing. Kerr et al. (1972) Br. J. Cancer, 26, 239-257; Wyllie et al. (1980) Int. Rev. Cytol., 68, 251-306. It plays an important role in normal tissue development and homeostasis, and defects in the apoptotic program are thought to contribute to a wide range of human disorders ranging from neurodegenerative and autoimmunity disorders to neoplasms. Thompson (1995) Science, 267, 1456-1462; Mullauer et al. (2001) Mutat. Res, 488, 211-231. Although the morphological characteristics of apoptotic cells are well characterized, the molecular pathways that regulate this process have only begun to be elucidated.

One group of proteins that is thought to play a key role in apoptosis is a family of cysteine proteases, termed caspases, which appear to be required for most pathways of apoptosis. Creagh & Martin (2001) Biochem. Soc. Trans, 29, 696-701; Dales et al. (2001) Leuk. Lymphoma, 41, 247-253. Caspases trigger apoptosis in response to apoptotic stimuli by cleaving various cellular proteins, which results in classic manifestations of apoptosis, including cell shrinkage, membrane blebbing and DNA fragmentation. Chang & Yang (2000) Microbiol. Mol. Biol. Rev., 64, 821-846.

Pro-apoptotic proteins, such as Bax or Bak, also play a key role in the apoptotic pathway by releasing caspase-activating molecules, such as mitochondrial cytochrome c, thereby promoting cell death through apoptosis. Martinou & Green (2001) Nat. Rev. Mol. Cell. Biol., 2, 63-67; Zou et al. (1997) Cell, 90, 405-413. Anti-apoptotic proteins, such as Bcl-2, promote cell survival by antagonizing the activity of the pro-apoptotic proteins, Bax and Bak. Tsujimoto (1998) Genes Cells, 3, 697-707; Kroemer (1997) Nature Med., 3, 614-620. The ratio of Bax:Bcl-2 is thought to be one way in which cell fate is determined; an excess of Bax promotes apoptosis and an excess of Bcl-2 promotes cell survival. Salomons et al. (1997) Int. J. Cancer, 71, 959-965; Wallace-Brodeur & Lowe (1999) Cell Mol. Life. Sci., 55, 64-75.

Another key protein involved in apoptosis is a protein that encoded by the tumor suppressor gene p53. This protein is a transcription factor that regulates cell growth and induces apoptosis in cells that are damaged and genetically unstable, presumably through up-regulation of Bax. Bold et al. (1997) Surgical Oncology, 6, 133-142; Ronen et al., 1996; Schuler & Green (2001) Biochem. Soc. Trans., 29, 684-688; Ryan et al. (2001) Curr. Opin. Cell Biol., 13, 332-337; Zörnig et al. (2001) Biochem. Biophys. Acta, 1551, F1-F37.

Alterations in the apoptotic pathways are believed to play a key role in a number of disease processes, including cancer. Wyllie et al. (1980) Int. Rev. Cytol., 68, 251-306; Thompson (1995) Science, 267, 1456-1462; Sen & D'Incalci (1992) FEBS Letters, 307, 122-127; McDonnell et al. (1995) Seminars in Cancer and Biology, 6, 53-60. Investigations into cancer development and progression have traditionally been focused on cellular proliferation. However, the important role that apoptosis plays in tumorigenesis has recently become apparent. In fact, much of what is now known about apoptosis has been learned using tumor models, since the control of apoptosis is invariably altered in some way in tumor cells. Bold et al. (1997) Surgical Oncology, 6, 133-142.

Cytokines also have been implicated in the apoptotic pathway. Biological systems require cellular interactions for their regulation, and cross-talk between cells generally involves a large variety of cytokines. Cytokines are mediators that are produced in response to a wide variety of stimuli by many different cell types. Cytokines are pleiotropic molecules that can exert many different effects on many different cell types, but are especially important in regulation of the immune response and hematopoietic cell proliferation and differentiation. The actions of cytokines on target cells can promote cell survival, proliferation, activation, differentiation, or apoptosis depending on the particular cytokine, relative concentration, and presence of other mediators.

The use of anti-cytokines to treat autoimmune disorders such as psoriasis, rheumatoid arthritis, and Crohn's disease is gaining popularity. The pro-inflammatory cytokines IL-1 and TNF play a large role in the pathology of these chronic disorders. Anti-cytokine therapies that reduce the biological activities of these two cytokines can provide therapeutic benefits (Dinarello and Abraham, 2002).

Interleukin 1 (IL-I) is an important cytokine that mediates local and systemic inflammatory reactions and which can synergize with TNF in the pathogenesis of many disorders, including vasculitis, osteoporosis, neurodegenerative disorders, diabetes, lupus nephritis, and autoimmune disorders such as rheumatoid arthritis. The importance of IL-1β in tumour angiogenesis and invasiveness was also recently demonstrated by the resistance of IL-1β knockout mice to metastases and angiogenesis when injected with melanoma cells (Voronov et al., 2003).

Interleukin 18 (IL-18) is a recently discovered member of the IL-1 family and is related by structure, receptors, and function to IL-1. IL-18 is a central cytokine involved in inflammatory and autoimmune disorders as a result of its ability to induce interferon-gamma (IFN-γ), TNF-α, and IL-1. IL-1β and IL-18 are both capable of inducing production of TNF-α, a cytokine known to contribute to cardiac dysfunction during myocardial ischemia (Maekawa et al., 2002). Inhibition of IL-18 by neutralization with an IL-18 binding protein was found to reduce ischemia-induced myocardial dysfunction in an ischemia/reperfusion model of suprafused human atrial myocardium (Dinarello, 2001). Neutralization of IL-18 using a mouse IL-18 binding protein was also able to decrease IFN-γ, TNF-α, and IL-1β transcript levels and reduce joint damage in a collagen-induced arthritis mouse model (Banda et al., 2003). A reduction of IL-18 production or availability may also prove beneficial to control metastatic cancer as injection of IL-18 binding protein in a mouse melanoma model successfully inhibited metastases (Carrascal et al., 2003). As a further indication of its importance as a pro-inflammatory cytokine, plasma levels of IL-18 were elevated in patients with chronic liver disease and increased levels were correlated with the severity of the disease (Ludwiczek et al., 2002). Similarly, IL-18 and TNF-α were elevated in the serum of diabetes mellitus patients with nephropathy (Moriwaki et al., 2003). Neuroinflammation following traumatic brain injury is also mediated by pro-inflammatory cytokines and inhibition of IL-18 by the IL-18 binding protein improved neurological recovery in mice following brain trauma (Yatsiv et al., 2002).

TNF-α, a member of the TNF family of cytokines, is a pro-inflammatory cytokine with pleiotropic effects ranging from co-mitogenic effects on hematopoietic cells, induction of inflammatory responses, and induction of cell death in many cell types. TNF-α is normally induced by bacterial lipopolysaccharides, parasites, viruses, malignant cells and cytokines and usually acts beneficially to protect cells from infection and cancer. However, inappropriate induction of TNF-α is a major contributor to disorders resulting from acute and chronic inflammation such as autoimmune disorders and can also contribute to cancer, AIDS, heart disease, and sepsis (reviewed by Aggarwal and Natarajan, 1996; Sharma and Anker, 2002). Experimental animal models of disease (i.e. septic shock and rheumatoid arthritis) as well as human disorders (i.e. inflammatory bowel diseases and acute graft-versus-host disease) have demonstrated the beneficial effects of blocking TNF-α (Wallach et al., 1999). Inhibition of TNF-α has also been effective in providing relief to patients suffering autoimmune disorders such as Crohn's disease (van Deventer, 1999) and rheumatoid arthritis (Richard-Miceli and Dougados, 2001). The ability of TNF-α to promote the survival and growth of B lymphocytes is also thought to play a role in the pathogenesis of B-cell chronic lymphocytic leukemia (B-CLL) and the levels of TNF-α being expressed by T cells in B-CLL was positively correlated with tumour mass and stage of the disease (Bojarska-Junak et al., 2002). Interleukin-1β (IL-1β) is a cytokine known to induce TNF-α production.

The amino acid sequence of eIF-5A is well conserved between species, and there is strict conservation of the amino acid sequence surrounding the hypusine residue in eIF-5A, which suggests that this modification may be important for survival. Park et al. (1993) Biofactors, 4, 95-104. This assumption is further supported by the observation that inactivation of both isoforms of eIF-5A found to date in yeast, or inactivation of the DHS gene, which catalyzes the first step in their activation, blocks cell division. Schnier et al. (1991) Mol. Cell. Biol., 11, 3105-3114; Sasaki et al. (1996) FEBS Lett., 384, 151-154; Park et al. (1998) J. Biol. Chem., 273, 1677-1683. However, depletion of eIF-5A protein in yeast resulted in only a small decrease in total protein synthesis suggesting that eIF-5A may be required for the translation of specific subsets of mRNA's rather than for protein global synthesis. Kang et al. (1993), "Effect of initiation factor eIF-5A depletion on cell proliferation and protein synthesis," in Tuite, M. (ed.), Protein Synthesis and Targeting in Yeast, NATO Series H. The recent finding that ligands that bind eIF-5A share highly conserved motifs also supports the importance of eIF-5A. Xu & Chen (2001) J. Biol. Chem., 276, 2555-2561. In addition, the hypusine residue of modified eIF-5A was found to be essential for sequence-specific binding to RNA, and binding did not provide protection from ribonucleases.

In addition, intracellular depletion of eIF-5A results in a significant accumulation of specific mRNAs in the nucleus, indicating that eIF-5A may be responsible for shuttling specific classes of mRNAs from the nucleus to the cytoplasm. Liu & Tartakoff (1997) Supplement to Molecular Biology of the Cell, 8, 426a. Abstract No. 2476, 37th American Society for Cell Biology Annual Meeting. The accumulation of eIF-5A at nuclear pore-associated intranuclear filaments and its interaction with a general nuclear export receptor further suggest that eIF-5A is a nucleocytoplasmic shuttle protein, rather than a component of polysomes. Rosorius et al. (1999) J. Cell Science, 112, 2369-2380.

The first cDNA for eIF-5A was cloned from human in 1989 by Smit-McBride et al., and since then cDNAs or genes for eIF-5A have been cloned from various eukaryotes including yeast, rat, chick embryo, alfalfa, and tomato. Smit-McBride et al. (1989) J. Biol. Chem., 264, 1578-1583; Schnier et al. (1991) (yeast); Sano, A. (1995) in Imahori, M. et al. (eds), Polyamines, Basic and Clinical Aspects, VNU Science Press, The Netherlands, 81-88 (rat); Rinaudo & Park (1992) FASEB J., 6, A453 (chick embryo); Pay et al. (1991) Plant Mol. Biol., 17, 927-929 (alfalfa); Wang et al. (2001) J. Biol. Chem., 276, 17541-17549 (tomato).

SUMMARY OF INVENTION

The present invention relates to apoptosis specific eucaryotic initiation factor 5A (eIF-5A), referred to as "apoptosis specific eIF-5A" or "eIF-5A1." The invention also relates to suppressing or inhibiting expression of pro-inflammatory cytokines in a subject, including a human, in vivo, (and in vitro in a cell) by inhibiting expression of apoptosis-specific eIF-5A through the use of eIF5A1 siRNAs or antisense polynucleotides. eIF5A1 siRNA and antisense constructs of eIF5A1 are administered to decrease expression of pro-inflammatory cytokines such as IL-1β, IL-2, IL-4, IL-5, IL-10, IFN-γ, TNF-α, IL-3, IL-6, IL-12(p40), IL-12(p70), G-CSF, KC, MIP-1α, and RANTES, which is useful in the treatment or prevention of sepsis and/or hemorrhagic induced shock.

The present invention also provides a pharmaceutical composition for decreasing expression of pro-inflammatory cytokines, comprising eIF5A1 siRNA and a pharmaceutically acceptable carrier. Pharmaceutical compositions of the invention may be administered to treat or prevent the onset of sepsis in a subject, including a human. In certain embodiments, the pharmaceutical composition comprises the nucleotide sequence

```
CGG AAU GAC UUC CAG CUG A (SEQ ID NO: 1).
```

BRIEF DESCRIPTION OF THE DRAWINGS

FIG. 1 shows that siRNA against eIF-5A1 causes decreased expression of IL-1β.

FIG. 19 provides an eIF-5A1 siRNA construct (SEQ ID NOS 3-5, respectively in order of appearance).

FIG. 22 provides the nucleotide sequence of human eIF5A1 (SEQ ID NO: 6) aligned against eIF5A2 (SEQ ID NO: 7).

FIG. 23 provides the amino acid sequence of human eIF5A1 (SEQ ID NO: 8) aligned against eIF5A2 (SEQ ID NO: 9).

FIG. 24 provides the nucleotide sequence of human eIF5A1 (SEQ ID NO: 16) with exemplary antisense oligonucleotides (SEQ ID NOS 10-15, respectively in order of appearance).

Figure 25:
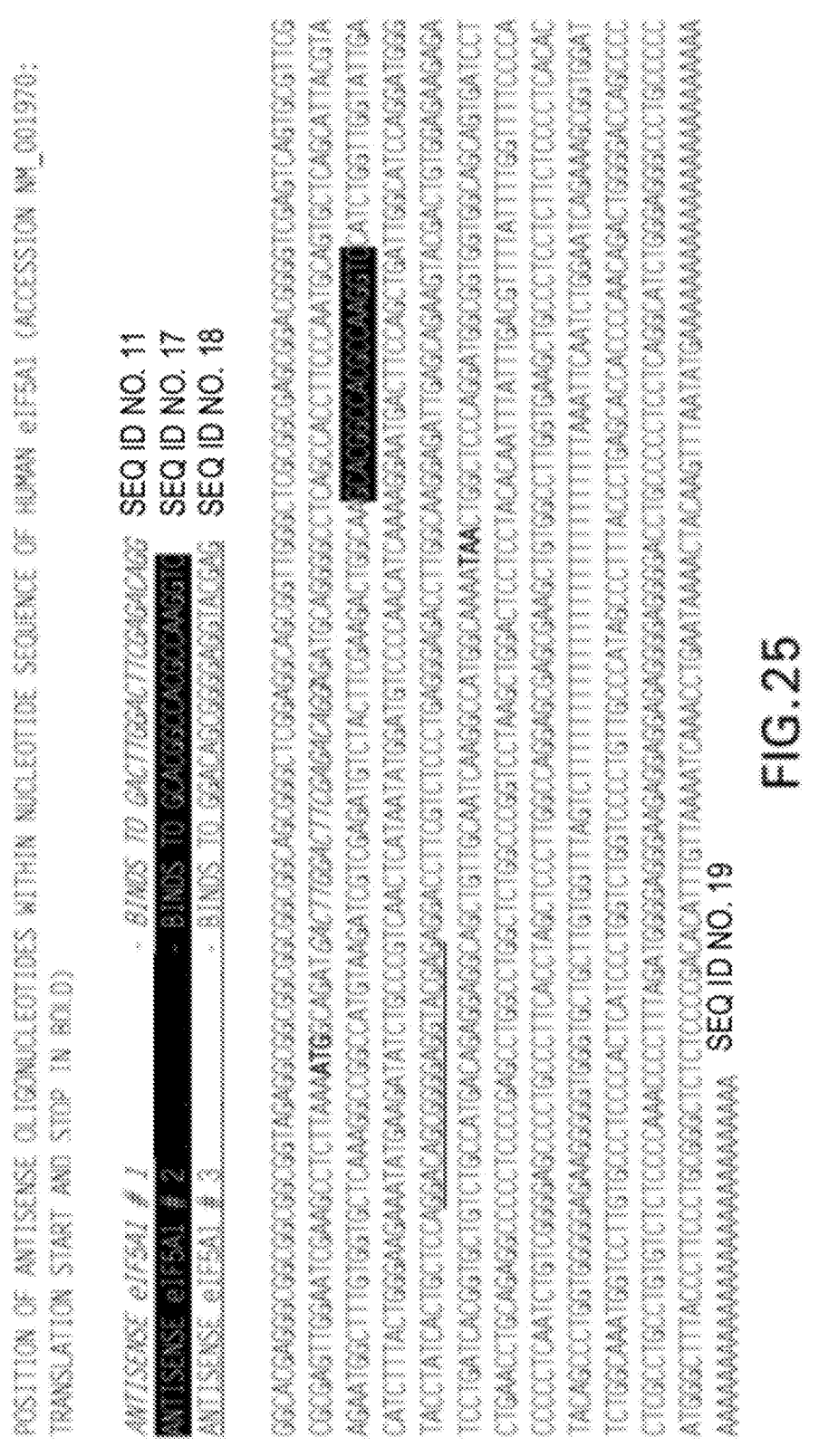

FIG. 25 provides the nucleotide sequence of human eIF5A1 (SEQ ID NO: 19) with exemplary antisense oligonucleotides (SEQ ID NOS 11 and 17-18, respectively in order of appearance).

FIGS. 26A and B provide the nucleotide sequence of human eIF5A1 (SEQ ID NO: 16) with exemplary siRNAs (SEQ ID NOS 20-34, respectively in order of appearance).

FIG. 27 provides the nucleotide sequence of human eIF5A1 (SEQ ID NO: 16) with exemplary siRNAs (SEQ ID NOS 35-39, respectively in order of appearance).

DETAILED DESCRIPTION OF THE INVENTION

Figure 1:
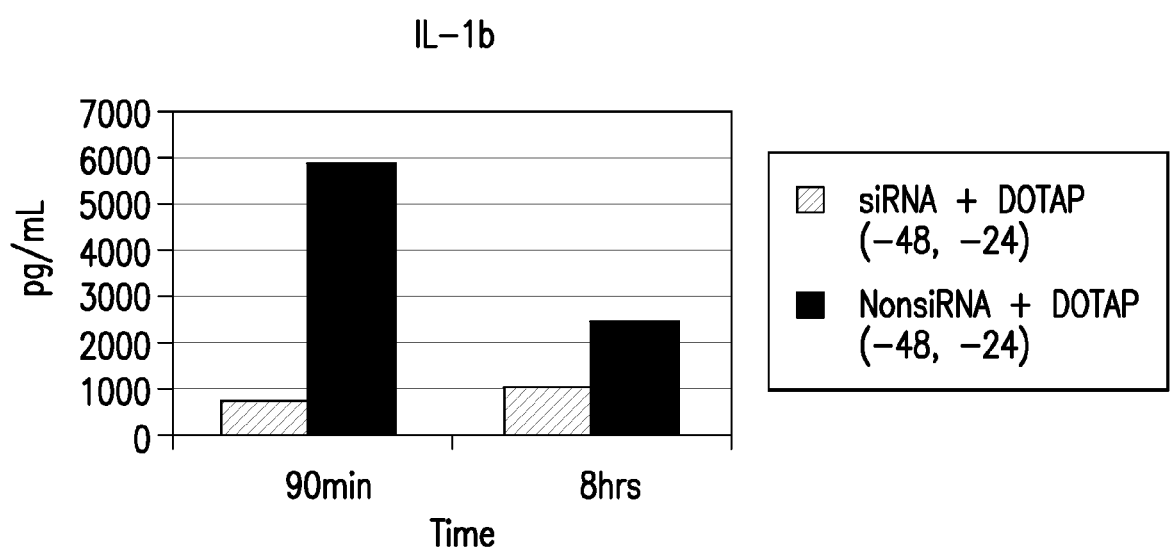
FIG. 1 shows the effects of siRNA against eIF-5A1 on the effect of proinflammatory cytokines.
Figure 2:
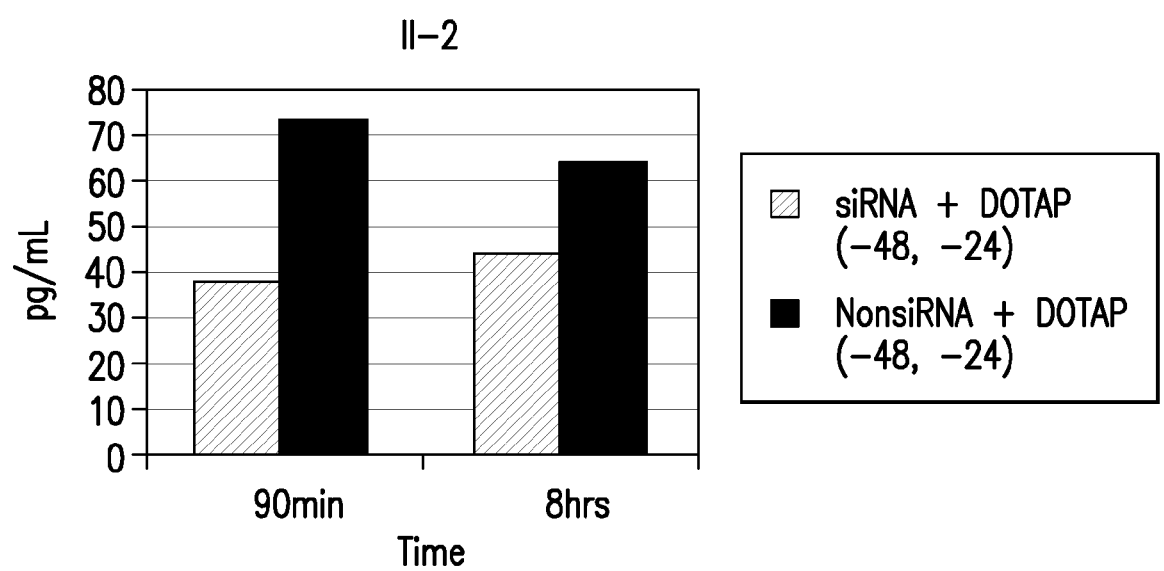
FIG. 2 shows that siRNA against eIF-5A1 causes decreased expression of IL-2.
Figure 3:
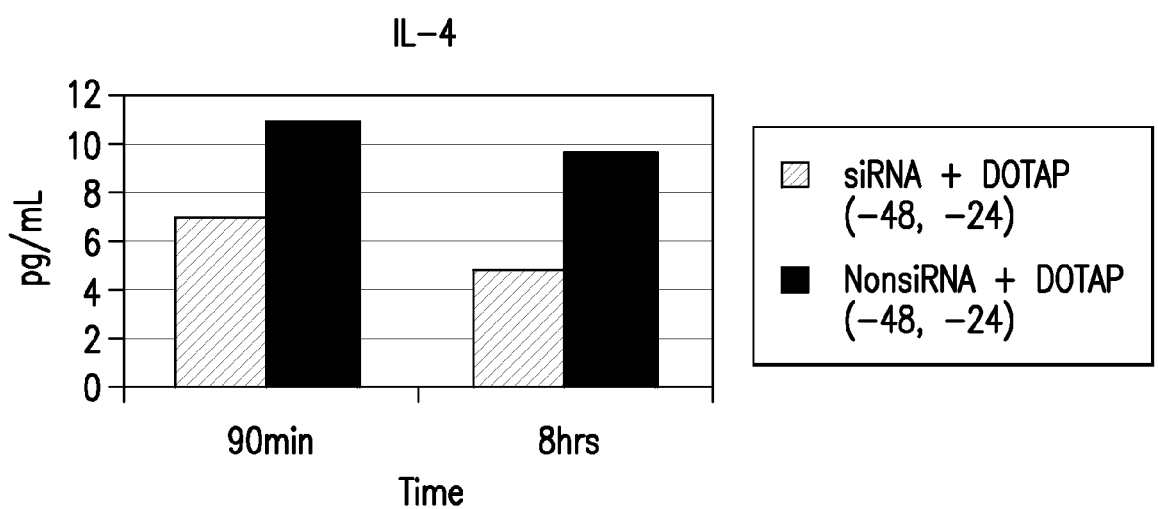
FIG. 3 shows that siRNA against eIF-5A1 causes decreased expression of IL-4.
Figure 4:
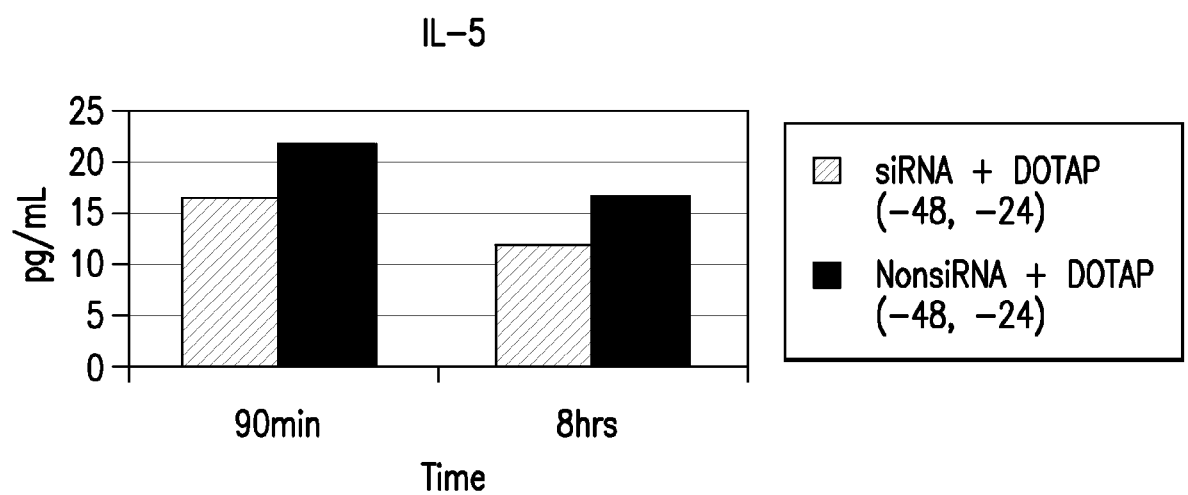
FIG. 4 shows that siRNA against eIF-5A1 causes decreased expression of IL-5.
Figure 5:
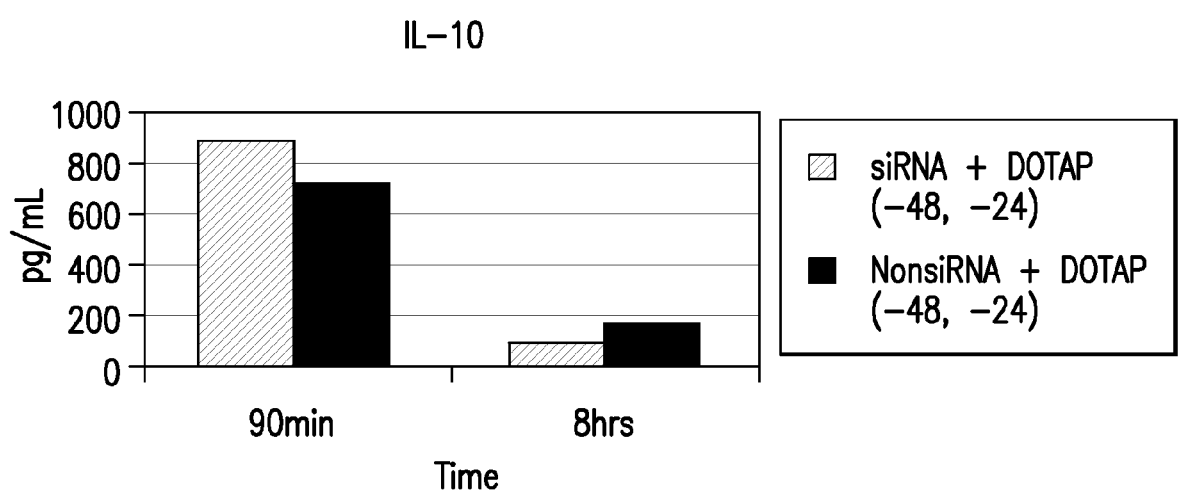
FIG. 5 shows that siRNA against eIF-5A1 causes decreased expression of IL-10.
Figure 6:
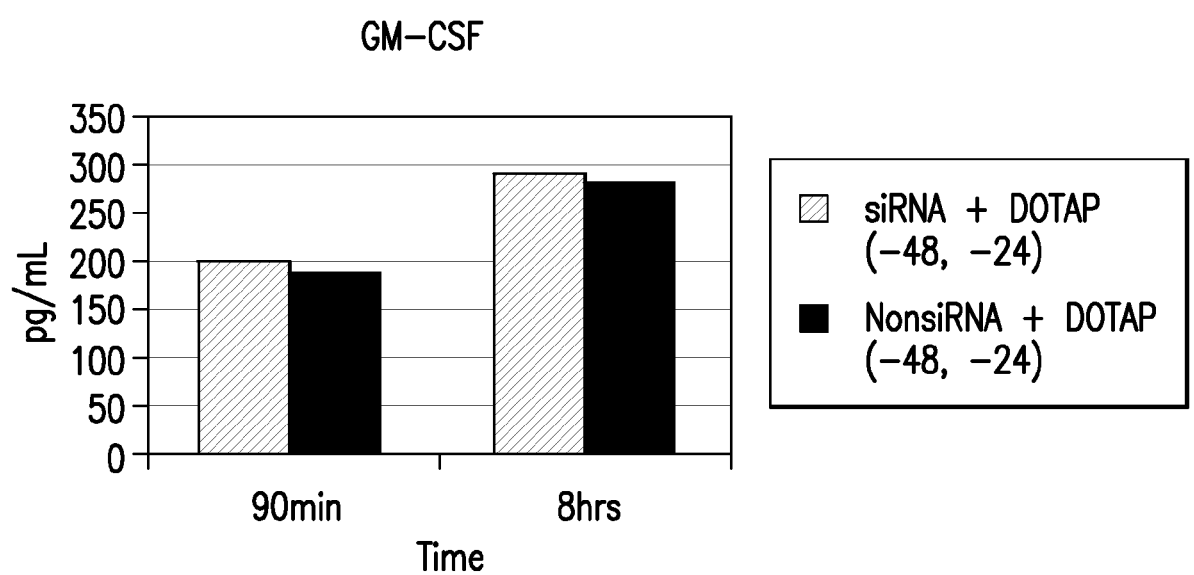
FIG. 6 shows that siRNA against eIF-5A1 causes increased expression of GM-CSF.
Figure 7:
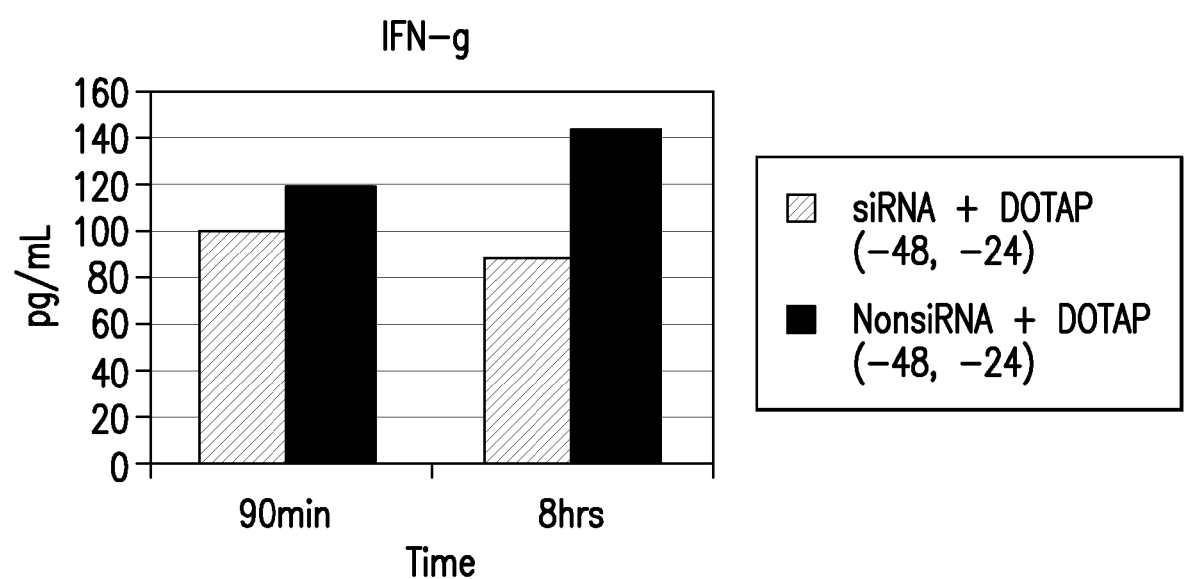
FIG. 7 shows that siRNA against eIF-5A1 causes decreased expression of IFN-γ.
Figure 8:
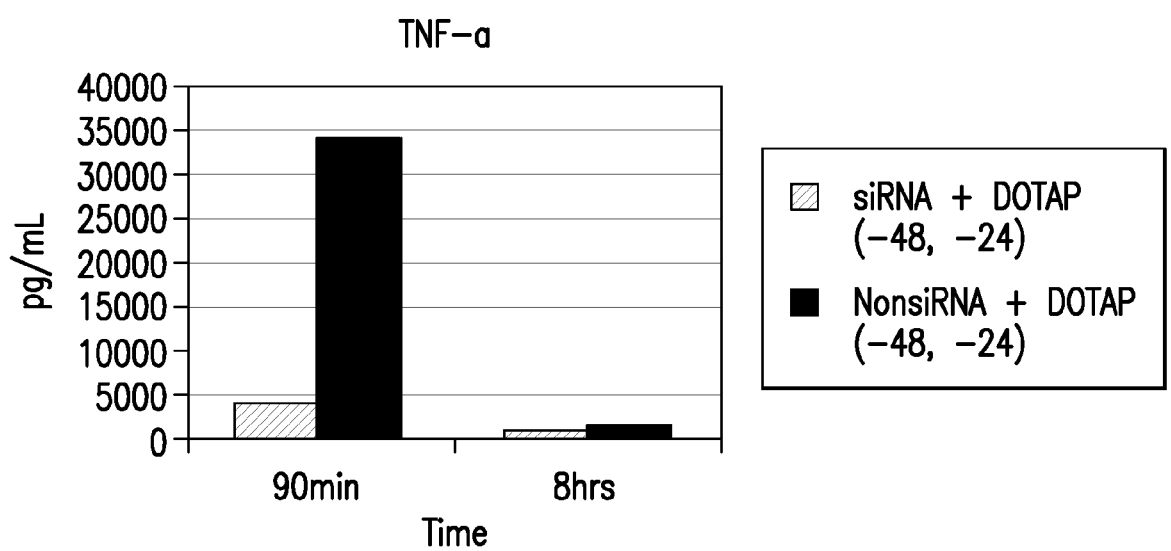
FIG. 8 shows that siRNA against eIF-5A1 causes decreased expression of TNF-α.
Figure 9:
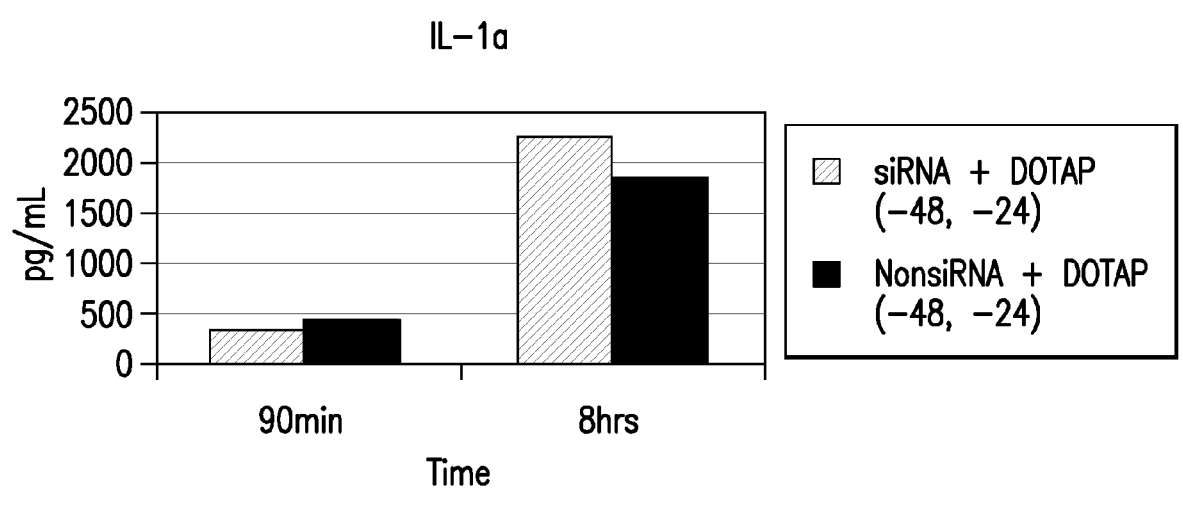
FIG. 9 shows that siRNA against eIF-5A1 causes increased expression of IL-1α.
Figure 10:
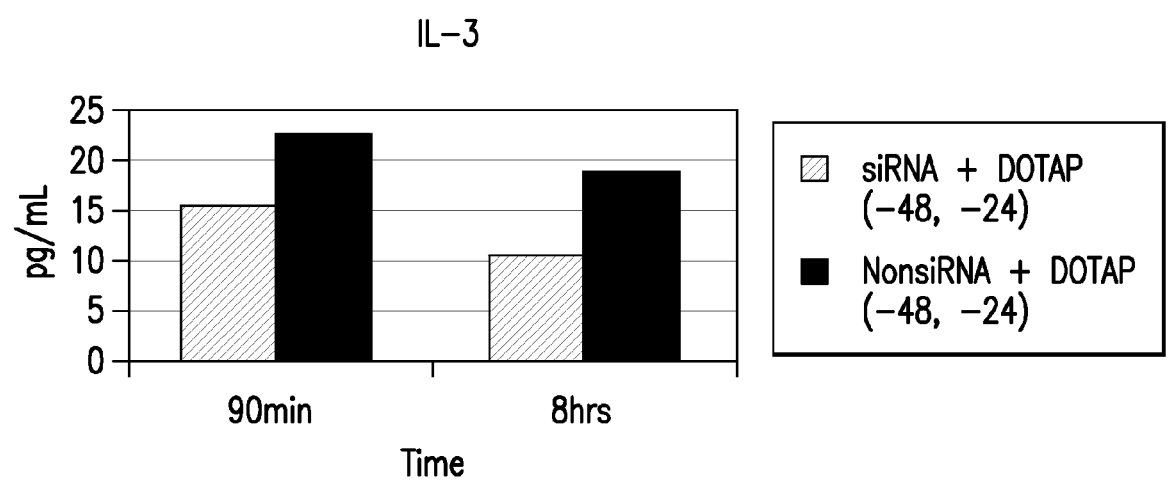
FIG. 10 shows that siRNA against eIF-5A1 causes decreased expression of IL-3.
Figure 11:
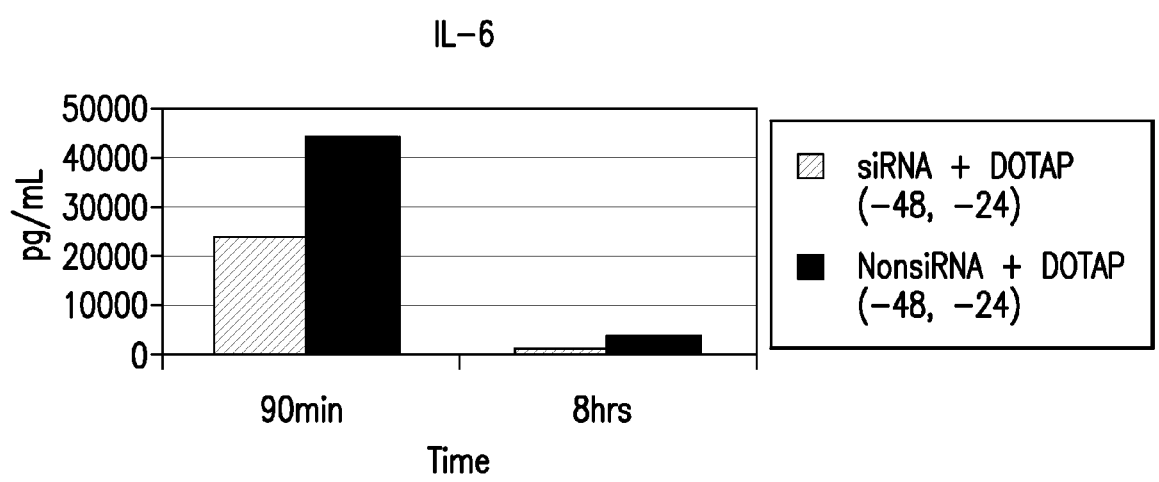
FIG. 11 shows that siRNA against eIF-5A1 causes decreased expression of IL-6.
Figure 12:
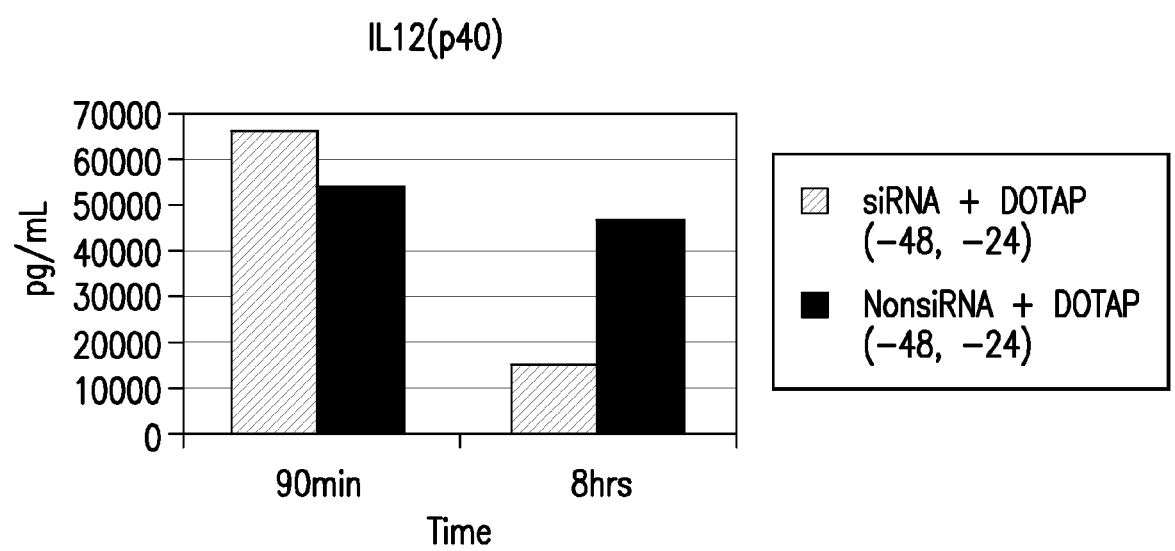
FIG. 12 shows that siRNA against eIF-5A1 causes decreased expression of IL-12(p40).
Figure 13:
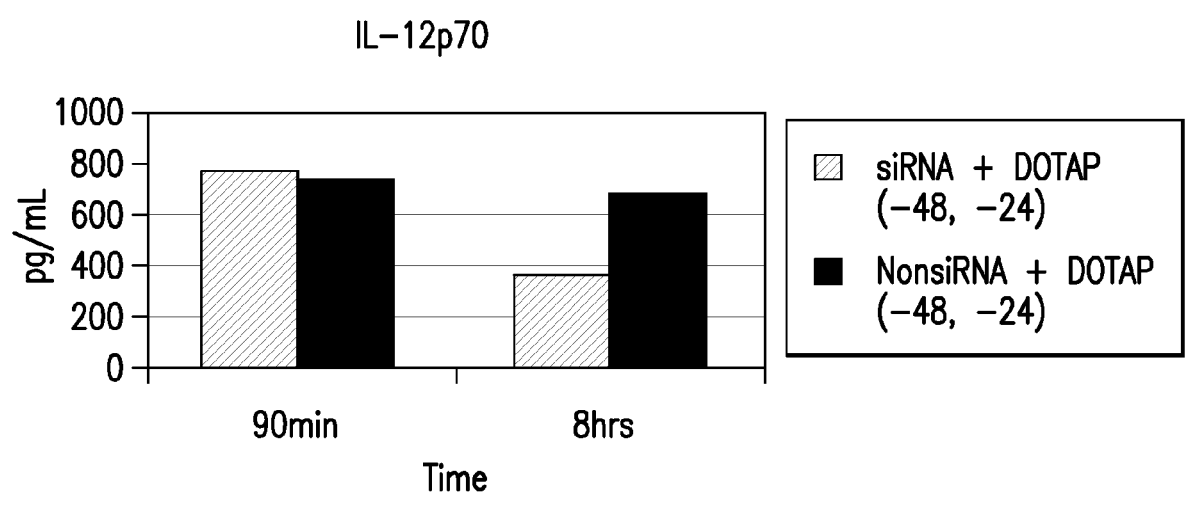
FIG. 13 shows that siRNA against eIF-5A1 causes decreased expression of IL-12(p70).
Figure 14:
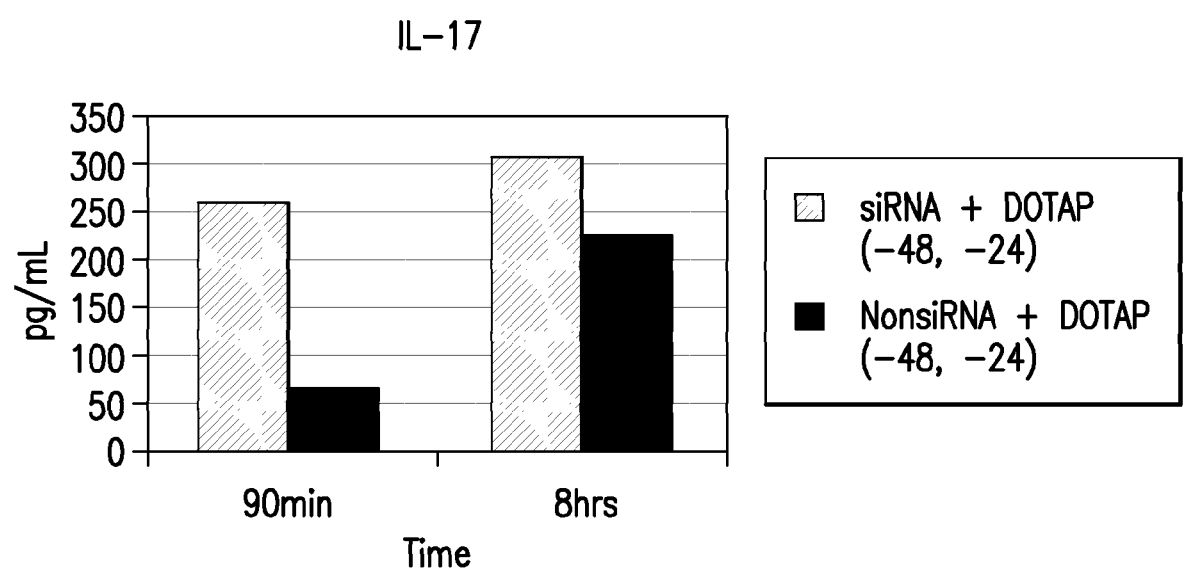
FIG. 14 shows that siRNA against eIF-5A1 causes increased expression of IL-17.
Figure 15:
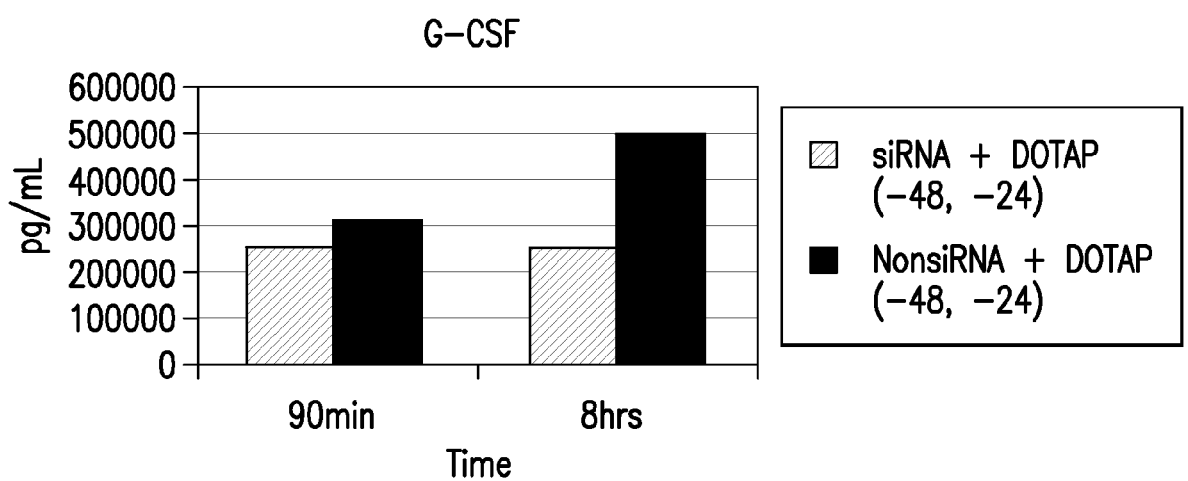
FIG. 15 shows that siRNA against eIF-5A1 causes decreased expression of G-CSF.
Figure 16:
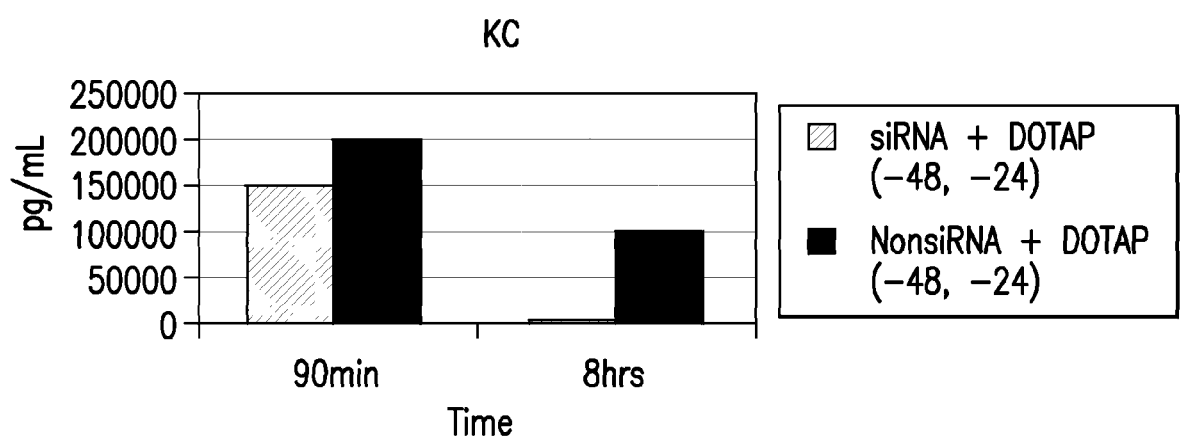
FIG. 16 shows that siRNA against eIF-5A1 causes decreased expression of KC.
Figure 17:
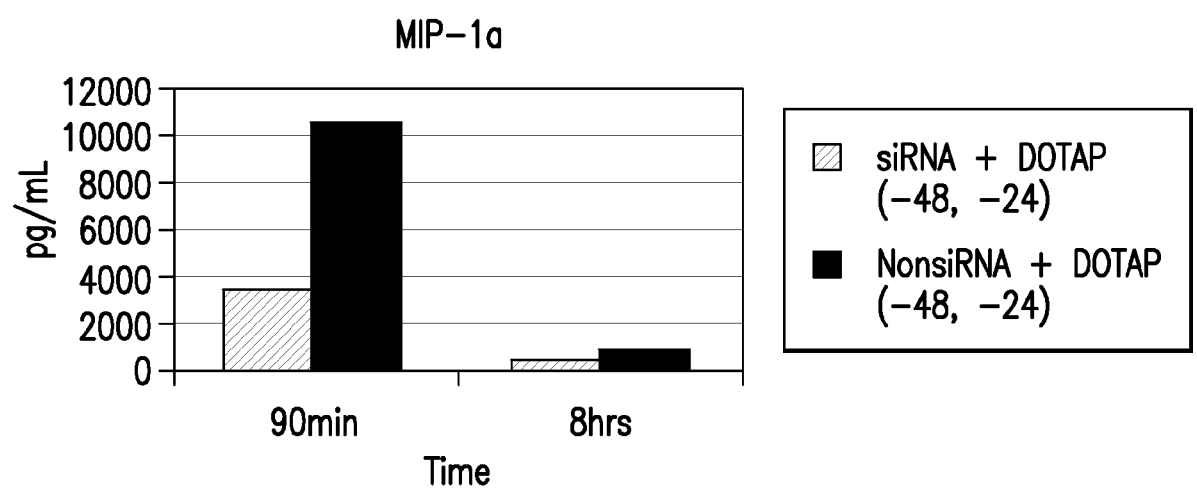
FIG. 17 shows that siRNA against eIF-5A1 causes decreased expression of MIP-1α.
Figure 18:
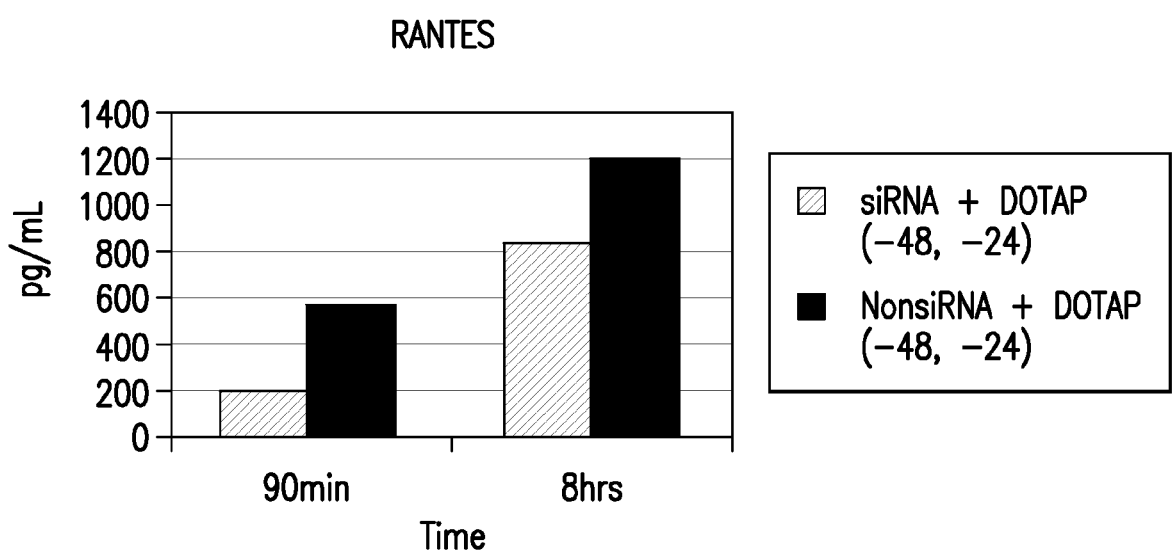
FIG. 18 shows that siRNA against eIF-5A1 causes decreased expression of RANTES.
Figure 20:
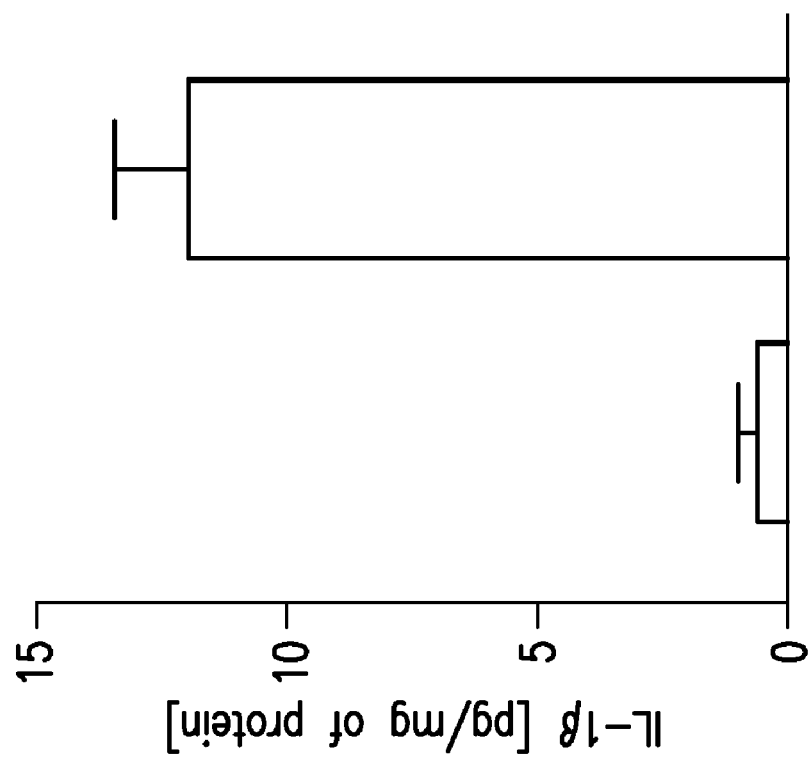
FIG. 20 shows the effect of cardiac puncture and bleeding on one hour post hemorrhagic lung. IL-1β expression significantly increases.

Several isoforms of eukaryotic initiation factor 5A ("eIF-5A") have been isolated and present in published databanks. It was thought that these isoforms were functionally redundant. The present inventors have discovered that one isoform is upregulated immediately before the induction of apoptosis, which they have designated apoptosis-specific eIF-5A or eIF-5A1. The subject of the present invention is apoptosis-specific eIF-5A and the down regulation of its expression to down regulate expression of pro-inflammatory cytokines.

Sepsis is a process of malignant intravascular inflammation causing ~210,000 deaths annually. Accordingly, adjunctive therapies are needed. Sepsis is also known as systemic inflammatory response syndrome ("SIRS"). Sepsis is caused by bacterial infection that can originate anywhere in the body. Sepsis can be simply defined as a spectrum of clinical conditions caused by the immune response of a patient to infection that is characterized by systemic inflammation and coagulation. It includes the full range of response from systemic inflammatory response (SIRS) to organ dysfunction to multiple organ failure and ultimately death.

Sepsis is a very complex sequence of events and much work still needs to be done to completely understand how a patient goes from SIRS to septic shock. Patients with septic shock have a biphasic immunological response. Initially they manifest an overwhelming inflammatory response to the infection. This is most likely due to the pro-inflammatory cytokines Tumor Necrosis Factor (TNF), IL-1, IL-12, Interferon gamma (IFN-γ), and IL-6. The body then regulates this response by producing anti-inflammatory cytokines (IL-10), soluble inhibitors (TNF receptors, IL-1 receptor type II, and IL-1RA (an inactive form of IL-1)), which is manifested in the patient by a period of immunodepression. Persistence of this hypo-responsiveness is associated with increased risk of nosocomial infection and death.

This systemic inflammatory cascade is initiated by various bacterial products. These bacterial products such as gram-negative bacteria=endotoxin, formyl peptides, exotoxins, and proteases; gram-positive bacteria=exotoxins, superantigens (toxic shock syndrome toxin (TSST), streptococcal pyrogenic exotoxin A (SpeA)), enterotoxins, hemolysins, peptidoglycans, and lipotechoic acid, and fungal cell wall material, which bind to cell receptors on the host's macrophages and activate regulatory proteins such as Nuclear Factor Kappa B (NFkB). Endotoxin activates the regulatory proteins by interacting with several receptors. The CD receptors pool the LPS-LPS binding protein complex on the surface of the cell and then the TLR receptors translate the signal into the cells.

As mentioned above, the pro-inflammatory cytokines produced are tumor necrosis factor (TNF), Interleukins 1, 6 and 12 and Interferon gamma (IFN-γ). These cytokines can act directly to affect organ function or they may act indirectly through secondary mediators. The secondary mediators include nitric oxide, thromboxanes, leukotrienes, platelet-activating factor, prostaglandins, and complement. TNF and IL-1 (as well as endotoxin) can also cause the release of tissue-factor by endothelial cells leading to fibrin deposition and disseminated intravascular coagulation (DIC).

These primary and secondary mediators then cause the activation of the coagulation cascade, the complement cascade and the production of prostaglandins and leukotrienes. Clots lodge in the blood vessels which lowers profusion of the organs and can lead to multiple organ system failure. In time, this activation of the coagulation cascade depletes the patient's ability to make a clot resulting in DIC and ARDS.

The cumulative effect of this cascade is an unbalanced state, with inflammation dominant over anti-inflammation and coagulation dominant over fibrinolysis. Microvascular thrombosis, hypoperfusion, ischemia, and tissue injury result. Severe sepsis, shock, and multiple organ dysfunction may occur, leading to death.

Because the present inventors had previously determined that eIF5A1 siRNA (delivered intranasaly as naked siRNA) decreased the production or expression of multiple potential mediators of sepsis (e.g. IL-1β, TNF-α, IL-8, iNOS, TLR-4 expression) in cell systems and a few proinflammatory cytokines in blood following intranasal lipopolysaccharide (LPS) challenge in vivo, the impact on survival and cytokine expression in endotoxemic mice was studied. See co-pending U.S. application Ser. Nos. 11/134,445 (filed May 23, 2005), 11/184,982 (filed Jul. 20, 2005), 11/293,391 (filed Nov. 28, 2005), and 11/595,990 (filed Nov. 13, 2006), which are all herein incorporated by reference in their entirety.

BALB/C mice were inoculated with *E. coli* O111:B4 LPS intraperitoneally (IP), causing death in 93% of controls. Animals received either eIF5A1 siRNA (N=5) (3'-GCC UUA CUG AAG GUC GAC U-5' (SEQ ID NO: 2)) or scrambled RNA as a control (N=15). A 50 µg dose of eIF5A1 siRNA was given IP in conjunction with 100 µg of transfection micelle comprised of DOTAP. The siRNA-liposome complex was dosed at t=−48 and −24 hrs prior to LPS administration. Survival experiments were conducted and under similar conditions mice were sacrificed at 90 min or 8 hours after LPS administration and blood sampled. A bead-based multiplex sandwich immunoassay quantified circulating cytokines. The results indicate that treatment of BALB/C mice with eIF5A1 siRNA conferred 60% protection (p<0.01). With treatment, IL-1β dropped from 5909 to 658 pg/mL at 90 min and from 2478 to 1032 pg/mL at 8 hrs. Treatment also decreased TNF-α from 33649 to 3696 pg/mL at 90 min and from 1272 to 901 at 8 hrs. MIP-1α also decreased from 10499 to 3475 pg/mL at 90 min and from 680 to 413 pg/mL at 8 hrs with treatment. At 8 hrs, treatment reduced IFN-γ from 142 to 86 pg/mL and IL-12(p40) from 46570 to 14261 pg/mL. The anti-inflammatory cytokine IL-10 was increased from 719 to 898 pg/mL at 90 min with treatment. These studies show that targeting inflammatory mediators with siRNA confers protection in endotoxemic mice and suggests this may be a useful approach in the treatment of septic patients.

In addition, to the septic model discussed above, the inventors also developed a novel murine model for studying hemorrhagic shock. In this model, male mice C-57BL/6J (8-12 weeks old) were induced into hemorrhage shock by withdrawal of 30% of the calculated blood volume (0.55 ml) by cardiac puncture over a 60-sec period (under methoxyflurane anesthesia). Lungs were harvested at 1 h after bleeding and were homogenized in 1 ml of ice-cold extraction buffer containing 20 mM HEPES (pH 7.4), 20 mM glycerophosphate, 20 mM sodium pyrophosphate, 0.2 mM $Na_3VO_4$, 2 mM EDTA, 20 mM sodium fluoride, 10 mM benzamidine, 1 mM DTT, 20 ng/ml leupeptin, 0.4 mM Pefabloc SC, and 0.01% Triton X-100. The homogenate was centrifuged at 14,000 g for 15 min at 4° C. The supernatant was collected, and the protein concentration was determined with the bicinchoninic acid assay. The resulting supernatant was used for determination of TNF, IL-1, and IL-6 by ECL (liquid phase ELISA), according to the manufacturer's suggestions. Final results were expressed as picograms cytokine protein per milligram of protein.

Figure 21:
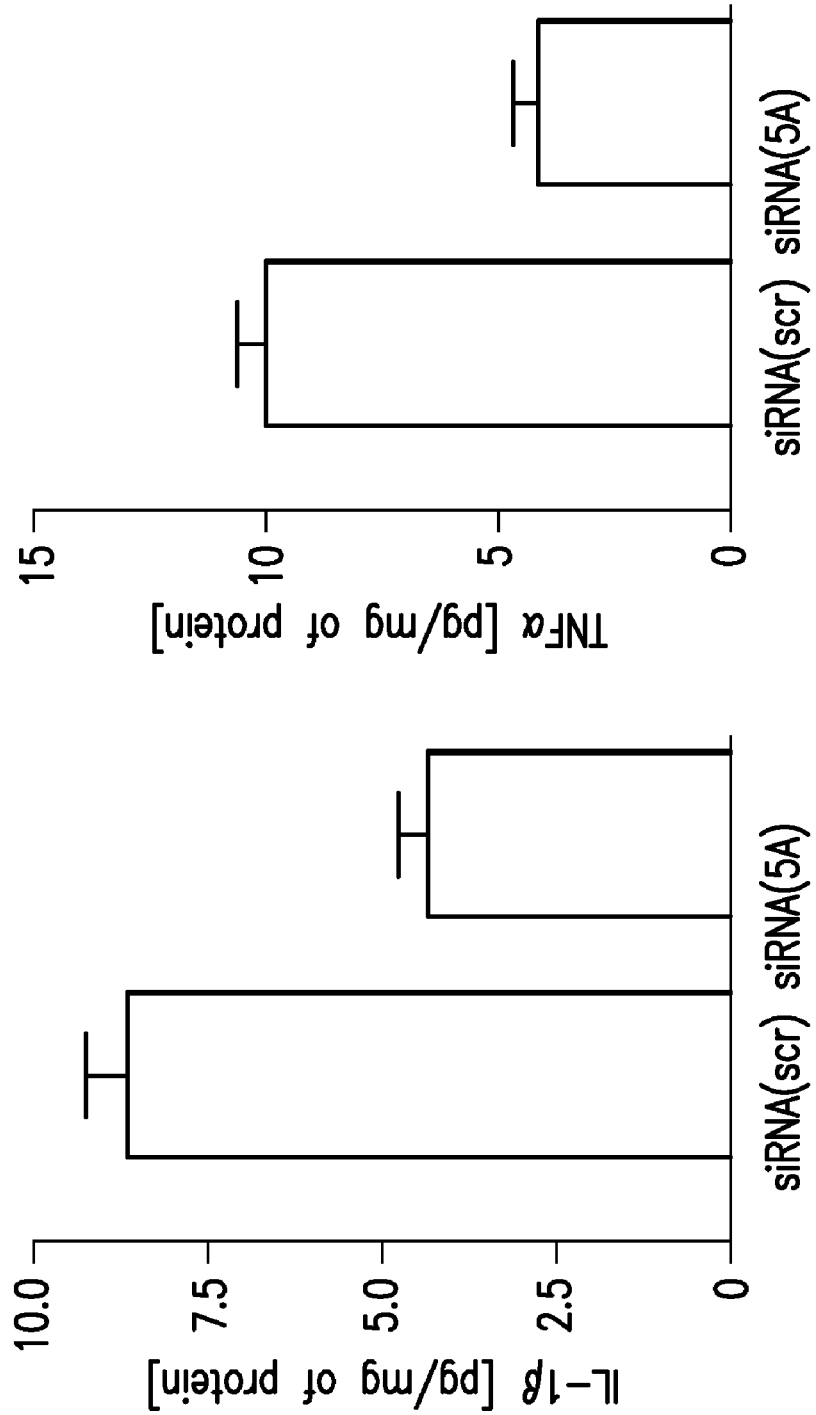
FIG. 21 shows that administration of eIF5A1 siRNA prior to inducement of hemorrhage shock, caused a decreased expression of Il-1B and TNF-α.

In another hemorrhagic model, the inventors showed that providing eIF5A siRNA, they could reducing expression of TNFα and IL-1β. 5 Mice C-57BL/6J, male induced i.p. were treated with 50 µg of eF5A1 siRNA 24 hours prior to hemorrhage. In the control, 5 Mice C-57BL/6J, male induced i.p. were treated with 50 µg of scrambled siRNA 24 hours prior to hemorrhage. Hemorrhage shock was developed by withdraw of 0.55 mL by cardiac puncture over a 60-sec period (under methoxyflurane-anesthesia). FIG. 21 shows that administration of siRNA prior to inducement of hemorrhage shock, provided a protective benefit by decreasing expression of Il-1β and TNF-α.

Thus, one embodiment of the present invention provides a method for decreasing expression of pro-inflammatory cytokines in vivo in a subject, comprising administering eIF5A1 siRNA to the subject, whereby the eIF5A1 siRNA decreases expression of pro-inflammatory cytokines. The subject may be any animal including a human.

The pro-inflammatory cytokine is any cytokine that is involved in the inflammation cascade, such as IL-1β, IL-2, IL-4, IL-5, IL-10, IFN-γ, TNF-α, IL-3, IL-6, IL-2(p40), IL-2 (p70), G-CSF, KC, MIP-1α, and RANTES. FIGS. 1-18 and 21-22 show that treatment with eIF5A1 siRNA resulted in a decreased amount of proinflammatory cytokines as compared to animals not having received the eIF5A1 siRNA.

As shown above, the inventors demonstrated that eIF5A siRNA confers protection in endotoxemic mice when pro-inflammatory cytokine expression was reduced. Hence, one embodiment of the invention also provides a method of treating sepsis in a subject by administering eIF5A1 siRNA to the subject, whereby administration of eIF5A1 siRNA decreases expression of eIF5A1 and results in decreased expression of pro-inflammatory cytokines. Decreased expression means reduced expression as well as decreased or reduced levels of a particular protein as compared to levels of expression or amounts of a protein in a subject not having been treated with eIF5A1 siRNA other eIF5A1 antisense constructs.

Another embodiment of the present invention further provides a method of preventing hemorrhagic shock in a subject, including a human, comprising administering an eIF5A1 siRNA or antisense polynucleotide to decrease expression of IL-1β and/or TNF-α.

Any eIF5A1 siRNA that inhibits expression of eIF5A1 may be used. The term "inhibits" also means reduce or decrease. One exemplary eIF5A1 siRNA comprises the sequence: CGG AAU GAC UUC CAG CUG A (SEQ ID NO: 1). Co-pending U.S. application Ser. Nos. 11/134,445 (filed May 23, 2005), 11/184,982 (filed Jul. 20, 2005), 11/293,391 (filed Nov. 28, 2005), and 11/595,990 (filed Nov. 13, 2006) (which are herein incorporated by reference in its entirety) provides additional exemplary eIF5A1 siRNAs and other antisense constructs that have been used to inhibit expression of eIF5A1 in other cell types and were also shown to inhibit expression of pro-inflammatory cytokines. One skilled in the art could design other eIF5A1 siRNAs given the eIF51A sequence and can easily test for the siRNAs ability to inhibit expression without undue experimentation. FIGS. 22-27 provide sequences of eIF5A1, exemplary eIF5A1 siRNAs and antisense constructs.

The preset invention also provides pharmaceutical compositions comprising eIF-5A1 siRNA or antisense polynucleotides discussed above useful for decreasing expression of pro-inflammatory cytokines. The composition may comprising eIF5A1 siRNA or antisense polynucleotides and a pharmaceutically acceptable carrier. Pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Generally, an effective amount of the eIF5A1 siRNA or eIF5A1 antisense nucleotides described above will be determined by the age, weight and condition or severity of disease of the recipient. Dosing may be one or more times daily, or less frequently. It should be noted that the present invention is not limited to any dosages recited herein.

Pharmaceutical compositions may be prepared as medicaments to be administered in any method suitable for the subject's condition, for example, orally, parenterally (including subcutaneous, intramuscular, and intravenous), rectally, transdermally, buccally, or nasally, or may be delivered to the eye as a liquid solution.

The siRNA or antisense construct can be delivered as "naked" siRNA or antisense nucleotide or may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The antisense polynucleotides and/or siRNA may be chemically modified. This may enhance their resistance to nucleases and may enhance their ability to enter cells. For example, phosphorothioate oligonucleotides may be used. Other deoxynucleotide analogs include methylphosphonates, phosphoramidates, phosphorodithioates, N3'P5'-phosphoramidates and oligoribonucleotide phosphorothioates and their 2'-O-alkyl analogs and 2'-O-methylribonucleotide methylphosphonates.

Alternatively mixed backbone oligonucleotides (MBOs) may be used. MBOs contain segments of phosphothioate oligodeoxynucleotides and appropriately placed segments of modified oligodeoxy- or oligoribonucleotides. MBOs have segments of phosphorothioate linkages and other segments of other modified oligonucleotides, such as methylphosphonate, which is non-ionic, and very resistant to nucleases or 2'-O-alkyloligoribonucleotides.

The invention claimed is:

1. A method of treating hemorrhagic shock in a subject comprising administering an eIF5A1 siRNA or eIFA1 antisense polynucleotide to decrease expression of IL-1β and/or TNF-α in the subject, thereby treating hemorrhagic shock.

2. The method of claim 1, wherein the eIF5A1 siRNA targets SEQ ID NO:29 of eIF5A1.

3. The method of claim 2 wherein the sense strand of siRNA comprises SEQ ID NO: 30 and the antisense strand comprises SEQ ID NO: 31.

4. The method of claim 2, further comprising administering a pharmaceutically acceptable carrier with the eIF5A1 siRNA or eIFA1 antisense polynucleotide.

5. The method of claim 1, wherein the expression of IL-1β is decreased in the subject.

6. The method of claim 1, wherein the expression of TNF-α is decreased in the subject.

7. The method of claim 1, wherein the subject is a human.

* * * * *